(12) United States Patent
O'Connor et al.

(10) Patent No.: US 7,022,313 B2
(45) Date of Patent: Apr. 4, 2006

(54) HYDROGEL PARTICLE FORMULATION

(75) Inventors: Barbara Horsey O'Connor, San Carlos, CA (US); Terry Lee Burkoth, Palo Alto, CA (US); Steven Joseph Prestrelski, Mountain View, CA (US); Yuh-Fun Maa, Millbrae, CA (US); Andrew Muddle, Oxon (GB); Roderick Hafner, Basingstoke (GB)

(73) Assignee: PowderJect Research Ltd., Oxford (GB)

( * ) Notice: Subject to any disclaimer, the term of this patent is extended or adjusted under 35 U.S.C. 154(b) by 444 days.

(21) Appl. No.: 09/922,218

(22) Filed: Aug. 3, 2001

(65) Prior Publication Data

US 2002/0061336 A1 May 23, 2002

Related U.S. Application Data

(63) Continuation of application No. PCT/GB00/00349, filed on Feb. 3, 2000
(60) Provisional application No. 60/118,334, filed on Feb. 3, 1999.

(51) Int. Cl.
*A61K 9/14* (2006.01)
*A61K 9/16* (2006.01)

(52) U.S. Cl. .................. 424/48; 424/499; 424/500; 424/501

(58) Field of Classification Search ......... 424/489–502, 424/422
See application file for complete search history.

(56) References Cited

U.S. PATENT DOCUMENTS

| | | | |
|---|---|---|---|
| 4,853,226 A | 8/1989 | Michida et al. | |
| 4,925,677 A | 5/1990 | Feijen | |
| 4,945,050 A | 7/1990 | Sanford et al. | |
| 4,978,069 A | 12/1990 | Anderson et al. | |
| 4,994,276 A | 2/1991 | Baichwal et al. | |
| 5,036,006 A | 7/1991 | Sanford et al. | |
| 5,041,292 A | 8/1991 | Feijen | |
| 5,053,332 A | 10/1991 | Cook et al. | |
| 5,630,796 A | 5/1997 | Bellhouse et al. | |
| 5,700,459 A | 12/1997 | Krone et al. | |
| 5,952,232 A | * 9/1999 | Rothman | 435/459 |

FOREIGN PATENT DOCUMENTS

| | | |
|---|---|---|
| EP | 0 357 401 | 3/1990 |
| EP | 0357401 A2 * | 7/1990 |
| GB | 2245831 A * | 1/1992 |
| GB | 2 245 831 | 1/1992 |
| WO | WO 91/07487 | 5/1991 |
| WO | WO 94/09819 | 5/1994 |
| WO | WO 94/24263 | 10/1994 |
| WO | WO 95/13798 | 5/1995 |
| WO | WO 98/13798 | 5/1995 |
| WO | WO 96/04947 | 2/1996 |
| WO | WO 96/12513 | 5/1996 |
| WO | WO 96/20022 | 7/1996 |
| WO | WO 96/25190 | 8/1996 |
| WO | WO 97/34652 | 9/1997 |
| WO | WO 97/48485 | 12/1997 |
| WO | WO 98/10750 | 3/1998 |
| WO | WO 99/01168 | 1/1999 |
| WO | WO 99/01169 | 1/1999 |
| WO | WO 00/13573 | 3/2000 |
| WO | WO 00/14547 | 3/2000 |
| WO | WO 00/15263 | 3/2000 |
| WO | WO 00/19982 | 4/2000 |
| WO | WO 00/43058 | 7/2000 |

OTHER PUBLICATIONS

Aasted, Bent, "Highly purified Agarose as Stacking Gel in Sodium Dodecyl Sulphate/Polyacrylamide–Gel Electrophoresis," *Biochem. J.* 189:183–184 (1980).

Albright et al., "Diet, Apoptosis, and Carcinogenesis," *Adv. Exper. Med. And Biol.* 422:92–107 (1997).

Cadic–Amadeuf et al., "Inflammatory Reaction Induced by Agarose Implants Reduced by Adding Adrenal Cells to the Polymer," *ASAIO Journal* 38(3);M386–M389 (1992).

Anderson and Hagel, "Some Properties and Applications of Superose 6B," *Analytical Biochemistry* 141:461–465 (1984).

Andrasko, Jan, "Water in Agarose Gels Studies by Nuclear Magnetic Resonance Relaxation in the Rotating Frame," *Biophys. Journal* 15(12):1235–1243 (1975).

Arndt, E.R. and Stevens, E. S., "Anhydro Sugar and Linkage Contributions to Circular Dichroism of Agarose and Carrageenan, With Conformational Implications," 303:73–78 (1997).

Arnott et al., "The Agarose Double Helix and Its Function in Agarose Gel Structure," *J. Mol. Biol.* 90:269–284 (1975).

Arshady, Reza, "Microspheres for Biomedical Applications: Preparation of Reactive and Labelled Microspheres," *Biomaterials* 14(1):5–15 (1993).

Artursson et al., "Biodegradable Microspheres, 1. Duration of Action of Dextranase Entrapped in Polyacrylstarch Microparticles in Vivo," *The Journal of Pharmacology and Experimental Therapeutics* 231(3):705–712 (1986).

Ayнкk et al., "Method of Obtaining Agarose from Agar–Agur," *Lab Delo* 6:370–371 (1976).

(Continued)

*Primary Examiner*—Gollamudi S. Kishore
(74) *Attorney, Agent, or Firm*—Foley & Lardner LLP

(57) ABSTRACT

New compositions formed from the combination of an active substance with a hydrogel carrier moiety are provided. The compositions are suitable for use in high-velocity transdermal particle injection techniques. Methods of providing the new compositions are also provided. In addition, methods for administering pharmacologically active agent to a subject are provided. These methods are useful for delivering drugs, biopharmaceuticals, vaccines and diagnostics agents.

15 Claims, 3 Drawing Sheets

OTHER PUBLICATIONS

Bourrillos, et al., "An Improved Method for Preparing Agarose," *Biochim. Biophys. Acta* 111:334–336 (1965).

Brogren, Carl–Henrik, "Brownian Motion and Electrophorectic Transport in Agarose Gels Studies by Epilfluorescence Microscopy and Single Particle Tracking Analysis," *J. Phys. Chem. B.* 101:5659–5663 (1997).

Bulone et al., "Mesoscopic Gels at Low Agarose Concentrations: Perturbation Effects of Ethanol," *Biophysical Journal* 72:388–395 (1997).

Muro–Cacho, Carlos A., "In Situ PCR: Overview of Procedures and Applications," *Frontiers in Bioscience* 2:15–19 (1997).

Chan et al., "An Inexpensive Solid Medium for Obtaining Colony–Forming Units of Oral Spirochetes," *Oral Microbiology Immunology* 12:372–376 (1997).

Coppi et al., "Polysaccharide Film–Coating Process for Freely Swellable Hydrogels," *Pharmaceutical Development and Technology* 3(3):347–353 (1998).

Cowan, D. E., "Thermophilic Proteins: stability and Function in Aqueous and Organic Solvents," *Comp. Biochem. Physiol.* 118A(3):429–438 (1997).

Davies et al., "Improved Manufacture and Application of an Agarose Magnetizable Solid–Phase Support," *Appl. Biochem. Biotechnol.* 68(1–2):95–112 (1997).

Davis, S.S. and Illum, L., "Polymeric Microspheres as Drug Carriers," *Biomaterials* 9(1):111–115 (1988).

Draye et al., "In vitro Characteristics of bioactive Molecules from Dextran Dialdehyde Cross–Linked Gelatin Hydrogel Films," *Biomaterials* 19:99–107 (1998).

Eppstein et al., "Alternative Delivery Systems for Peptides and Proteins As Drugs," *CRC Critical Reviews in Therapeutic Drug Carrier System* 5(2):99–139 (1998).

Gehrke et al., "Enhanced Loading and Activity Retention of Bioactive Proteins in Hydrogel Delivery Systems," *Journal of Controlled Release* 55:21–33 (1998).

Gombotz, W. and Pettit, DK., "Biodegradable Polymers for Protein and Peptide Drug Delivery," *Bioconjugate Chem.* 6(4):332–351 (1995).

Gribnau et al., "Microscopic Observations on Commercial Sepharose Deviations From Normal Bead–Structure," *FEBS Letters* 57(3):301–303 (1975).

Gustavsson et al., "Superporous Agarose Beads as a Hydrophobic Interaction Chromatography Support," *Journal of Chromatography A* 830:275–284 (1999).

Gustavsson et al., Continuous Superporous Agarose Beds for Chromatography and Electrophoresis, *Journal of Chromatography A* 832:29–39 (1999).

Häglund et al., "Dissolution Controlled Drug Release From Agarose Beads," *Drug Development and Industrial Pharmacy* 20(6):947–959 (1994).

Hjertén, S. and Liao, J., "High–Performance Liquid Chromatography of Proteins on Compressed, Non–Porous Agarose Beads," *Journal of Chromatography* 457:165–174 (1988).

Holloway et al., "Agarose–Encapsulated Adsorbents," *The International Journal of Artificial Organs* 2(1):81–86 (1979).

Howe, F.A., "Relaxation times in Paramagnetically Doped Agarose Gels as a Function of Temperature and Ion Concentration," *Magnetic Resonance Imaging* 6:263–270 (1988).

Ito et al., "Quantitative Prediction of in Vitro Drug Clearance and Drug Interactions from in Vitro data on Metabolism, Together with Binding and Transport," *Annu. Rev. Pharmacol. Toxicol.* 38:461–499 (1998).

Frank–Kamenetskii, M., " A Simple Solution to the Stability of the Double Helix?," *Nature* 324:p. 305 (1986).

Kanke et al., "Clearance of $^{141}$Ce–Labeled Microspheres from Blood and Distribution in Specific Organs Following Intravenous and Intraarterial Administration in Beagle Dogs," *Journal of Pharmaceutical Sciences* 69(7):755–762 (1980).

Kim et al., "Hydrogels: Swelling, Drug Loading, and Release," *Pharmaceutical Research* 9(3):283–290 (1992).

Kikuchi et al., "Effect of $Ca^{2+}$ –Alginate Gel Dissolution on Release on Dextran with Different Molecular Weights," *Journal of Controlled Release* 58:21–28 (1999).

Jani, G.K., and Gohel, M.C., "Effects of Selected formulation Parameters on the Entraptment of Diclofenac Sodium in Ethyl Cellulose Microspheres," *Journal of Controlled Release* 43:245–250 (1997).

Kuijpers et al., "Controlled Delivery of Antibacterial Proteins From Biodegradable Matrices," *Journal of Controlled Release* 53:235–247 (1998).

Li et al., "High–Performance Liquid Chromatography of Proteins on Deformed NonPorous Agarose Beads. Affinity Chromatography of Dehydrogenases Based on Cibacron Blue–Derivatized Agarose," *Preparative Biochemistry* 20(2):107–121 (1990).

Lösgen et al., "Large Agarose Beads for Extracorporeal Detoxification System," *Biomat. Med. Dev. Art. Org.* 6(2):151–173 (1978).

Lundberg, P. and Kuchel, P.W., "Diffusion of Solutes in Agarose and Alginate Gels: $^1H$ and $^{23}Na$ PFGSE and $^{23}Na$ TQF NMR Studies," *Mag. Res. Med.* 37(1):44–52 (1997).

Maaloum et al., "Agarose Gel Structure Using Atomic Force Microscopy: Gel concentration and Ionic Strength Effects," *Electrophoresis* 19:1606–1610 (1998).

Margel, S., "Agarose–Polyaldehyde Microsphere Beads: Synthesis and Biomedical Applications," *Applied Biochemistry and Biotechnology* 8:523–539 (1983).

Margel, S., and Offarim, M., "Novel Effective Immunoadsorbents Based on Agarose–Polyaidehyde Microsphere Beads: Synthesis and Affinity Chromatography," *Analytical Biochemistry* 128:342–350 (1983).

McNeil, M.E. and Graham N. G., "Properties Controlling the Difusion and Release of Water–Soluble Solutes from Poly(Ethylene Oxide) Hydrogels: 3.Device Geometry," *J. Biomater. Sci. Polymer Edn.* 7(11):937–951 (1996).

Mitsuiki et al., j"Determination of Molecular Weight of Agars and Effect of the Molecular Weight on the Glass Transition," *J. Agric. Food Chem.* 47:473–478 (1999).

Moussaoui et al., "Diffusion of Proteins in Sepharose Cl–B Gels," *Journal of Chromatography* 591:115–120 (1992).

Nunjeri et al., "Hydrogel Beads Based on Amidated Pectins for Colon–Specific Drug Delivery: The Role of Chitosan in Modifying Drug Release," *Journal of Controlled Release* 46:273–278 (1997).

Munjeri et al., "An Investigation into the Suitability of Amidated Pectin Hydrogel Beads as a Delivery Matrix for Chloroquine," *Journal of Pharmaceutical Sciences* 87(8):905–908 (1998).

Nakano et al., "Agarose–Encapsulated Adsorbent Beads for Direct Hemoperfusion: Preparation and in Vitro Evaluation," *Chem. Parm. Buil.* 342:2591–2598 (1986).

Okada et al., "Medical Application of Microencapsulating Hybridoma Cells in Agarose Microbeads "Cytomedicine": Therapeutic Effect on igG1 Plasmacytosis and Mesangio-–Proliferative Glomerulonephritis in the Interleukin 6 Transgenic Mouse," *Journal of Controlled Release 44*:195–200 (1997).

Okada, H. and Toguchi, H., "Biodegradable Microspheres in Drug Delivery," *Critical Reviews in Therapeutic Drug Carrier Systems 12*(1):1–99 (1995).

Patil, R. and Speaker, T.J., "Water–Based Microsphere Delivery System for Proteins," *Journal of Pharmaceutical Sciences 89*(1):9–15 (2000).

Patil et al., "Macroporous Poly(Sucrose Acrylate) Hydrogel for Controlled Release of Macromolecules," *Biomaterials 17*(24):2343–2350 (1996).

Pernodet et al., "Pore Size of Agarose Gels by Atomic Force Microscopy," *Electrophoresis 18*:55–58 (1997).

Polson et al., "Preparation of Agarose with Low Net Negative Charge Density Using an Expensive Anion Exchanger," *Preparative Biochemistry 16*(4):309–319 (1986).

Polson et al., "Agarose: A Possible Universal Gel Exclusion Agent," *Preparative Biochemistry 14*(2):173–179 (1984).

Ramzi et al., "Structure–Properties Relation for Agarose Thermoeversible Gels in Binary Solvents," *Macromolecules 31*:6106–6111 (1998).

Rees, D. A., "Structure Confirmation and Mechanism in the Formation of Polysaccharide Gels and Networks," *Advances in Carbohydr. Chem Biochem. 24*:3 + 7–332 (1969).

Schroeder et al., "Distribution of radiolabeled Subvision Microspheres After Intravenous Administration to Beagle Dogs," *J. Pharm. Sci. 67*(4):504–509 (1978).

Schroeder et al., "Physiological Effect of Subvision Microspheres Administered to Beagle Dogs," *J. Pharm. Sci. 67*(4):508–513 (1978).

Sideman et al., "Tailor–Made Agarose–Based Reactive Beads for Hemoperfusion and Plasma Perfusion," *Applied Biochemistry Biotechnology 10*:167–182 (1984).

Sjöbert et al., "How Interactions Between Drugs and Agaros–Carrageenan Hydrogels Influence the Simultaneous Transport of Drugs," *Journal of Controlled Release 59*:391–400 (1999).

Stellwagen, J. and Stellwagen, N.C., "The Effect of Gel Structure on Matrix Orientation," *Electrophoresis 13*:595–600 (1992).

Stenekes, R.J.H. and Hennik, W.E., "Equilibrium Water Content of Microspheres Based on Cross–Linked Dextran," *International Journal of Pharmaceutics 189*:131–135 (1999).

Tanaka, Toyoichi, *Gels* 124–138.

Thano et al., "Biodegradable Indium–111 Labeled Microspheres for in Vivo Evaluation of Distribution and Elimination," *Pharmaceuticals Research 12*(12):2060–2064 (1995).

Vanbever et al., "Formulation and Physical Characterization of Large Porous Particles for Inhalation," 16(11):1735–1741 (1999).

Waki, S. and Harvey, J.D., "Study of Agarose Gels by Electro Microscopy of Freeze–Fractured Surfaces," *Biopolymers* 21:1909–1926 (1982).

Walker et al., "Preparation of Agarose Gels as Reference Substances for NMR Relaxation Time Measurement," *Magnetic Resonance Imaging 6*:215–222 (1988).

White, K.N., *Tanpakushitu Kakusan Koso 221*(13):1431–1436 (1977).

* cited by examiner

HYDROGEL PARTICLE FORMULATION

This application is a continuation of International Patent Application No. PCT/BG00/00349, filed Feb. 3, 2000, designating the United States, from which priority is claimed pursuant to 35 USC 120, and also claims priority from U.S. Provisional Application No. 60/118,334, filed Feb. 3, 1999, which applications are incorporated by reference.

TECHNICAL FIELD

The present invention relates generally to particulate pharmaceutical compositions. More particularly, the invention pertains to particulate pharmaceutical compositions that are suitable for transdermal particle delivery from a needleless syringe system, and to methods for producing such compositions.

BACKGROUND OF THE INVENTION

The ability to deliver pharmaceuticals agents into and through skin surfaces (transdermal delivery) provides many advantages over oral or parenteral delivery techniques. In particular, transdermal delivery provides a safe, convenient and noninvasive alternative to traditional administration systems, conveniently avoiding the major problems associated with oral delivery (e.g. variable rates of absorption and metabolism, gastrointestinal irritation and/or bitter or unpleasant drug tastes) or parenteral delivery (e.g. needle pain, the risk of introducing infection to treated individuals, the risk of contamination or infection of health care workers caused by accidental needle-sticks and the disposal of used needles).

However, despite its clear advantages, transdermal delivery presents a number of its own inherent logistical problems. Passive delivery through intact skin necessarily entails the transport of molecules through a number of structurally different tissues, including the stratum corneum, the viable epidermis, the papillary dermis and the capillary walls in order for the drug to gain entry into the blood or lymph system. Transdermal delivery systems must therefore be able to overcome the various resistances presented by each type of tissue.

In light of the above, a number of alternatives to passive transdermal delivery have been developed. These alternatives include the use of skin penetration enhancing agents, or "permeation enhancers," to increase skin permeability, as well as non-chemical modes such as the use of iontophoresis, electroporation or ultrasound. However, these alternative techniques often give rise to their own unique side effects such as skin irritation or sensitization. Thus, the spectrum of agents that can be safely and effectively administered using traditional transdermal delivery methods has remained limited.

More recently, a novel transdermal drug delivery system that entails the use of a needleless syringe to fire powders (i.e., solid drug-containing particles) in controlled doses into and through intact skin has been described. In particular, commonly owned U.S. Pat. No. 5,630,796 to Bellhouse et al describes a needleless syringe that delivers pharmaceutical particles entrained in a supersonic gas flow. The needleless syringe is used for transdermal delivery of powdered drug compounds and compositions, for delivery of genetic material into living cells (e.g., gene therapy) and for the delivery of biopharmaceuticals to skin, muscle, blood or lymph. The needleless syringe can also be used in conjunction with surgery to deliver drugs and biologics to organ surfaces, solid tumors and/or to surgical cavities (e.g., tumor beds or cavities after tumor resection). In theory, practically any pharmaceutical agent that can be prepared in a substantially solid, particulate form can be safely and easily delivered using such devices.

Hydrogel compositions are well-known in the biomedical arts, and are commonly used as substrates for cell and tissue culture, impression materials for prosthetics, wound-packing materials, or as solid phase materials in size exclusion or affinity chromatography applications. For example, nonporous, deformed and/or derivatized agarose hydrogel compositions have been used in high-performance liquid chromatography and affinity chromatography methods (Li et al (1990) *Preparative Biochem.* 20:107–121), and superporous agarose hydrogel beads have been used as a support in hydrophobic interaction chromatography (Gustavsson et al (1999) *J. Chromatography* 830:275–284). In the pharmaceutical fields, hydrogel monomers (natural or synthetic) are commonly added to pharmaceutical compositions (with an initiator and, sometimes, cross-inking agents) and then allowed to polymerize, thereby encapsulating a guest pharmaceutical within a hydrogel matrix. These techniques are used to provide microsphere carrier systems for drug targeting or controlled release systems. For example, cross-linked hydrogel microspheres have been used to encapsulate islet cells for the treatment of diabetes (Lim et al (1980) *Science* 210:908–910) or cancer cells that produce cancer-suppressing materials (U.S. Pat. No. 5,888,497), and biodegradable hydrogel microspheres are widely used to encapsulate a wide variety of drug compositions, most commonly peptides and proteins (Wang et al (1997) *Pharm. Dev. and Technology* 2:135–142). In these applications, the particular hydrogel system employed in the formulation is selected to provide long-term entrapment of the guest cell or pharmaceutical substance (e.g., to provide for targeted delivery or sustained- or delayed-release pharmacokinetics).

SUMMARY OF THE INVENTION

This invention is based on the discovery that pharmacologically-active agents can be associated with hydrogel particles for transdermal particle injection into a subject, particularly a human. The composition is in the form of a powder that comprises materials including a suitable pharmacologically-active agent associated with a hydrogel particles, wherein the particles that make up the powder have an average cross-sectional dimension of about 0.1 to 250 microns, preferably about 10 microns to 100 microns, i.e., 10 to 100 μm mass mean aerodynamic diameter in size.

The composition finds use with a device that effects the direct injection of the composition into or through skin, muscle or tissue, e.g. across the stratum corneum or into transmucosal membranes, thus defeating their barrier functions. Generally this is achieved by accelerating the particles in a transient supersonic helium gas jet to velocities of 100–3000 meters/second. The pharmacological agents included with the hydrogel include drugs (i.e., small organic molecules), biopharmaceuticals (i.e., peptides, larger proteins, and oligonucleotides), traditional and DNA vaccines, and gene therapies that provide a biochemical and physiological effect on the subject to which it is being administered. The effect may be such that it prevents or ameliorates a disease in the man or animal treated. The advantages of the invention include easy processing, high loading of the active agent, and a narrow-size distribution of the particles within the composition.

Accordingly, the present invention provides use of a pharmacologically active agent in the manufacture of a particulate medicament also comprising a hydrogel, for use in the therapeutic treatment of a subject by particle injection.

The invention also provides a method for making a powdered pharmaceutical composition suitable for administration by particle injection, said method comprising:
(a) contacting hydrogel particles with an aqueous composition containing a pharmacologically active agent, thereby to load the particles with the agent;
(b) optionally, separating the thus loaded hydrogel particles from the aqueous composition in an at least partial drying step and contacting the separated particles with an aqueous composition containing said pharmacologically active agent, thereby to load further the particles with the agent;
(c) if step (b) has been carried out, optionally repeating said step one or more times such as from one to twenty times;
(d) separating the thus loaded hydrogel particles from the aqueous composition in a drying step; and
(e) obtaining the desired powdered pharmaceutical composition suitable for use in a transdermal powder injection device.

In one embodiment of the invention, a particulate medicament consisting essentially of a hydrogel loaded with an expressible gene construct encoding an antigen can be used as a nucleic acid for delivery to a subject by particle injection. In another embodiment, a particulate medicament consisting essentially of a hydrogel loaded with an antigen can be used as a vaccine for delivery to a subject by particle injection.

It is an advantage of the present invention that hydrogel particles can be used as carrier systems for pharmacologically active guest agents, thereby facilitating high-velocity particle injection delivery performance of such agents. Since release of the guest agent will typically be dependent upon factors such as: degree of swelling experienced by the hydrogel when delivered to an aqueous environment; dissolution of a crystallized guest agent; the cross-linking density of the hydrogel matrix; diffusion of the active from the hydrogel matrix; degradation of the hydrogel matrix; and the like, numerous delivery profiles can be readily tailored for each guest agent. In addition, the methods for loading preformed hydrogel beads with a guest substance allows for presizing of the hydrogel carriers prior to loading of expensive active ingredients, thus avoiding possible loss of such agent upon typical particle sizing operations.

These and other objects, aspects, embodiments and advantages of the present invention will readily occur to those of ordinary skill in the art in view of the disclosure herein.

DETAILED DESCRIPTION OF THE PREFERRED EMBODIMENTS

Figure 1:
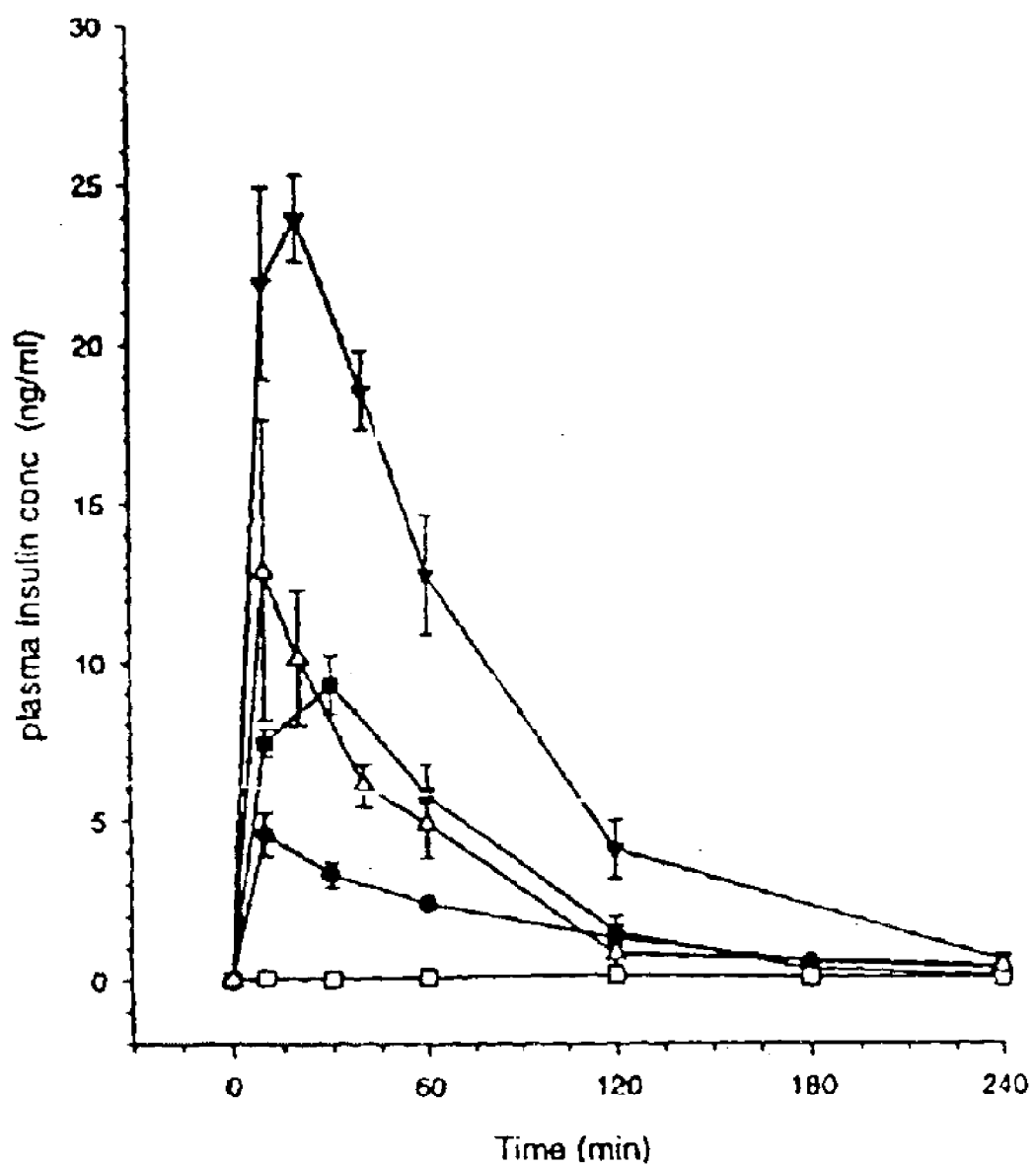
FIG. 1 shows the mean (±S.E.) plasma insulin concentration vs time profiles obtained in Example 1 following dermal particle injection (DPJ) administration of: standard lyophilised formulation (■, 287 µg/kg), agarose bead formulation CG 0904 (▼, 353 µg/kg), agarose bead formulation CG 0920 ∆, 421 µg/kg), and placebo formulation (□, 0 µg/kg). Subcutaneous insulin administration (●, 28.3 µg/kg) is shown for comparison.

Before describing the present invention in detail, it is to be understood that this invention is not limited to particularly exemplified hydrogel or pharmaceutical powder formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a particle" includes a mixture of two or more such particles, reference to "a pharmaceutical" includes mixtures of two or more such agents, and the like.

A. Definitions

Unless defined otherwise, all technical and scientific terms used herein have the same meaning as commonly understood by one of ordinary skill in the art to which the invention pertains. The following terms are intended to be defined as indicated below.

In describing the present invention, the following terms will be employed, and are intended to be defined as indicated below.

The term "powder" as used herein refers to a composition that consists of substantially solid particles that can be delivered transdermally using a needleless syringe device. The particles that make up the powder can be characterized on the basis of a number of parameters including, but not limited to, average particle size, average particle density, particle morphology (e.g. particle aerodynamic shape and particle surface characteristics) and particle penetration energy (P.E.).

The average particle size of the powders according to the present invention can vary widely and is generally from 0.1 to 250 µm, for example from 10 to 100 µm and more typically from 20 to 70 µm. The average particle size of the powder can be measured as a mass mean aerodynamic diameter (MMAD) using conventional techniques such as microscopic techniques (where particles are sized directly and individually rather than grouped statistically), absorption of gases, permeability or time of flight. If desired, automatic particle-size counters can be used (e.g. Aerosizer Counter, Coulter Counter, HIAC Counter, or Gelman Automatic Particle Counter) to ascertain the average particle size.

Actual particle density or "absolute density" can be readily ascertained using known quantification techniques such as helium pycnometry and the like. Alternatively, envelope ("tap") density measurements can be used to assess the density of a powder according to the invention. The envelope density of a powder of the invention is generally from 0.1 to 25 $g/cm^3$, preferably from 0.8 to 1.5 $g/cm^3$.

Envelope density information is particularly useful in characterizing the density of objects of irregular size and shape. Envelope density is the mass of an object divided by its volume, where the volume includes that of its pores and small cavities but excludes interstitial space. A number of methods of determining envelope density are known in the art, including wax immersion, mercury displacement, water absorption and apparent specific gravity techniques. A number of suitable devices are also available for determining envelope density, for example, the GeoPyc™ Model 1360, available from the Micromeritics Instrument Corp. The difference between the absolute density and envelope density of a sample pharmaceutical composition provides information about the sample's percentage total porosity and specific pore volume.

Particle morphology, particularly the aerodynamic shape of a particle, can be readily assessed using standard light microscopy. It is preferred that the particles which make up the instant powders have a substantially spherical or at least substantially elliptical aerodynamic shape. It is also preferred that the particles have an axis ratio of 3 or less to avoid the presence of rod- or needle-shaped particles. These same microscopic techniques can also be used to assess the particle surface characteristics, e.g. the amount and extent of surface voids or degree of porosity.

Particle penetration energies can be ascertained using a number of conventional techniques, for example a metallized film P.E. test. A metallized film material (e.g. a 125 µm polyester film having a 350 Å layer of aluminum deposited on a single side) is used as a substrate into which the powder is fired from a needleless syringe (e.g. the needleless syringe described in U.S. Pat. No. 5,630,796 to Bellhouse et al) at an initial velocity of about 100 to 3000 m/sec. The metallized film is placed, with the metal coated side facing upwards, on a suitable surface.

A needleless syringe loaded with a powder is placed with its spacer contacting the film, and then fired. Residual powder is removed from the metallized film surface using a suitable solvent. Penetration energy is then assessed using a BioRad Model GS-700 imaging densitometer to scan the metallized film, and a personal computer with a SCSI interface and loaded with MultiAnalyst software (BioRad) and Matlab software (Release 5.1, The MathWorks, Inc.) is used to assess the densitometer reading. A program is used to process the densitometer scans made using either the transmittance or reflectance method of the densitometer. The penetration energy of the powders should be equivalent to, or better than that of reprocessed mannitol particles of the same size (mannitol particles that are freeze-dried, compressed, ground and sieved according to the methods of commonly owned International Publication No. WO 97/48485, incorporated herein by reference).

The term "subject" refers to any member of the subphylum cordata including, without limitation, humans and other primates including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The methods described herein are intended for use in any of the above vertebrate species, since the immune systems of all of these vertebrates operate similarly.

The term "transdermal delivery" includes both transdermal ("percutaneous") and transmucosal routes of administration, i.e. delivery by passage through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987).

B. General Methods

A medicament is thus provided comprising solid particles of about 0.1 to about 250 microns (µm) in average diameter, preferably about 10 to about 100 µm in average diameter, where each particle comprises a hydrogel structure having associated therewith a pharmacologically-active agent, the particles being suitable for transdermal delivery to a subject by particle injection. In some embodiments, the size of the particles is about 20 to about 75 µm and more preferably about 40 to about 60 µm in average diameter. The character of the particles is sufficient to withstand the ballistic impact with the target skin, tissue or mucosal surface upon the delivery from a needleless syringe as well as the interaction of the particles within the delivery device. The composition is in the form of a powder that may be produced in bulk, transported in containers or prepared as a unit dosage for use with a needleless syringe delivery device, i.e. a needleless syringe.

Hydrogels Useful in the Invention

The hydrogels useful in this invention are those that are pharmaceutically-acceptable in the subject to which the composition will be administered. The hydrogels should be stable over time in the dehydrated form. The hydrogels may be naturally-occurring (e.g., agarose and alginate) or may be synthetically prepared or modified (e.g., polyethylene glycol PEG). A hydrogel is a material comprising a macromolecular three-dimensional network that allows it to swell when in the presence of water, to shrink in the absence of (or by reduction of the amount of) water but not dissolve in water. The swelling, i.e., the absorption of water, is a consequence of the presence of hydrophilic functional groups attached to or dispersed within the macromolecular network. Cross-inks between adjacent macromolecules result in the aqueous insolubility of these hydrogels. The cross-links may be due to chemical (i.e., covalent) or physical (i.e., Van Der Waal forces, hydrogen-bonding, ionic forces, etc.) bonds. While some in the polymer industry may refer to the macromolecular material useful in this invention as a "xerogel" in the dry state and a "hydrogel" in the hydrated state, for purposes of this patent application the term "hydrogel" will refer to the macromolecular material whether dehydrated or hydrated. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

Typically, a pharmacologically-active agent is associated with the hydrogel through aqueous dispersal of the agent in the macromolecular network and the material is then dried to immobilize and entrap the agent in the hydrogel. The association of the agent with the hydrogel may be a uniform dispersion and absorption throughout the resulting hydrogel particle or a partial dispersion in only part of the hydrogen particle. Additionally or alternatively, the association of the agent with the hydrogel may be due to ionic or covalent bonds formed between the two components, and the agent may be contained primarily within the hydrogel matrix or associated with (e.g., bonded to) the surface of the hydrogel structure. Preferably the agent is essentially fully absorbed into the macromolecular network of the hydrogel. The association of the agent with the hydrogel may take place during the formation of the hydrogel particles or after the particles have been prepared. Once the hydrogel composition is administered into the skin or mucosal site, the agent is released to the animal's system by one of several mechanisms. Once the hydrogel is in an aqueous environment, the macromolecular network will expand, thus releasing the agent and/or, if the macromolecular network is biodegradable, it will erode and release the compound. Thus, the hydrogel can be non-biodegradable (i.e., transportable and excretable) or it will be bio-degradable (i.e., erodible). The erodible hydrogel generally may be viewed as two types: (1) erodible at the cross-links, or (2) erodible at the backbone.

Synthetically prepared hydrogels generally will be prepared by polymerizing a monomeric material to form a backbone and cross-inking the backbone with a cross-linking agent. Common hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide.

Some synthetic hydrogels are made by free radical polymerization of hydrophilic vinyl monomers. The initiation step is the formation of a free radical, usually by the addition of azo-type initiators such as 2,2'-azobis(2-methylpropanenitrile) or peroxide initiators such as benzoyl peroxide. Ultraviolet light or gamma radiation can also initiate the reaction. Propagation takes place by free radical reaction with the vinyl monomer groups. Normally a portion of the reaction mixture consists of difunctional vinyl compounds that provide a degree of cross-linking. The hydrophilicity of the gel is usually controlled by copolymerizing a hydrophilic and hydrophobic vinyl monomer into the gel. The permeability of a hydrogel is determined, i.a., by the extent of cross-linking, the degree of hydration of the gel, and the nature of the permeant.

The quantity and type of solvent used in the polymerization mix can substantially affect the quality of the gel produced. For example, poly(hydroxyethyl methacrylate), or poly(HEMA), only absorbs 35–40 wt % of water, and therefore poly(HEMA) prepared from polymerization reaction mixtures containing a greater amount of water contain water-filled voids and are translucent or opaque in appearance. Cross-linking usually reduces the water sorption of the polymer.

Hydrogels may also be prepared in the absence of water and subsequently equilibrated with water or with a concentrated aqueous solution of the active agent. Care must be taken to avoid preparing highly hydrophilic hydrogels having a high degree of cross-linking in the dry state, since equilibration with water may then induce internal pressures that can result in mechanical fracture of a hydrogel structure. Other parameters to be controlled in the preparation of hydrogels are the temperature of polymerization and concentration of the initiator.

Examples of hydrogels that are erodible include those prepared from polyvinyl alcohol, hydroxyethyl methacrylate, polyacrylic acid, polyoxyethylene, polylactic-co-glycolic acid, and the like. Erodible hydrogels where the hydrolytic instability resides in the cross links include a cross-linked product prepared by copolymerizing N-vinylpyrrolidone or acrylamide with N,N'-methylenebisacrylamide. Erodible hydrogels where the hydrolytic instability resides in the backbone links are prepared by condensing an unsaturated diacid (e.g. fumaric) with a diol (e.g. poly(ethylene glycol)) and cross linking with vinylpyrrolidone in a free radical reaction.

Further discussion of synthetic hydrogels may be found at "*Controlled Release of Biologically Active Agents*" by Richard Baker, A Wiley-Interscience Publication, John Wiley & Sons, pp. 101–104 and 178–183. This reference is incorporated herein by reference.

While hydrogels find many uses in pharmaceutical, biomedical and biotechnology applications, none have been used in the manner described in this invention. A discussion of hydrogel applications may be found in the following publications:

BIODEGRADABLE HYDROGELS FOR DRUG DELIVERY BIODEGRADABLE HYDROGELS FOR DRUG DELIVERY,

Kinam Park, Waleed S. W. Shalaby, and Haesun Park (July 1993)

HYDROGELS: SPECIALITY PLASTICS FOR BIOMEDICAL AND PARMACEUTICAL APPLICATION (Ringbou edition) (July 1990)

HYDROGELS AND BIODEGRADABLE POLYMERS FOR BIOAPPLICANTS (ASC SYMPOSIUM SERIES, 627) (June 1996)

HYDROGELS IN MEDICINE AND PHARMACY: FUNDAMENTALS

Nikolaos Peppas

HYDROGELS IN MEDICINE AND PHARMACY: POLYMERS

Nikolaos Peppas (Editor) (February 1987)

HYDROGELS IN MEDICINE AND PHARMACY: PROPERTIES AND AAPPLICATIONS

Nikolaos Peppas (Editor) (June 1987)

Naturally occurring hydrogels useful in this invention include various polysaccharides available from natural sources such as plants, algae, fungi, yeasts, marine invertebrates and arthropods. Representative examples include agarose, dextrans, chitin, cellulose-based compounds, starch, derivatised starch, and the like. These generally will have repeating glucose units as a major portion of the polysaccharide backbone. Agarose and dextrans are preferred.

Agarose is the neutral gelling fraction of agar, a polysaccharide complex extracted from the agarocytes of algae of the *Rhodophyceae*. Predominant agar-producing genera are *Gelidium, Gracclaria, Acanthopeltis, Ceramium* and *Pterocladia* found in the Pacific and Indian Oceans and the Japan Sea. Agarose has found wide use as a chromatography resin and as such is widely available for use in chromatography columns. The material is available from various sources under different tradenames as very fine particles (beads) having a tightly controlled diameter size of anywhere from 10 to 100 μm. As used herein, the term "bead" is used in its normal biochemical sense to refer to small, discrete hydrogel particles. Agarose beads suitable for use herein are widely available from, for example, Sigma Chemical Company (St. Louis, Mo.), Prometic Biosciences, Inc. (Montreal, Quebec, Canada), and Bio-Rad Corporation (Hercules, Calif.) as Bio-Gel A15M. Alternatively, suitable agarose beads (e.g., 4%, 6%, 8% and higher agarose w/v concentration, cross linked or non-cross linked) can be readily formed using a number of known techniques. For example, agarose beads can be formed by spraying agarose into "ice-cold" ether (Hjerten, S. (1964) *Biochem. Biophys. Acta* 79:393–398), using warm non-aqueous solvents into which agarose is emulsified prior to gel formation on cooling (U.S. Pat. No. 5,053,332), by dropwise addition of hot agarose solution into chilled mineral oil and water (U.S. Pat. No. 5,053,332), by dropping agarose solution onto a chilled hydrophobic surface (U.S. Pat. No. 5,053,332), or by dropping agarose solution onto a spinning disk (U.S. Pat. No. 4,978,069). These later "solvent-free" formation methods are preferred herein.

Dextran is a polysaccharide produced by bacteria growing on a sucrose substrate, containing a backbone of D-glucose units linked predominantly α-D(1→6). Several organisms produce dextrans but only *Leuconostoc mesenteroides* and *L. dextranicum (Lactobacteriaceac)* have been used commercially. Native dextrans with high molecular weight are preferred. All dextrans are composed exclusively of α-D-glucopyranosyl units. Tradenames of high molecular weight dextrans above 70,000 mw include Dextran 70, Hyskon, Macrodex and Dextran 75, Gentran 75. Dextrans can be modified to form, e.g., polidexide, also known as dextran 2-(diethylamino) ethyl 2-[[2-(diethamino)ethyl]-diethylammonio] ethyl ether chloride hydrochloride epichlorohydrin crosslinked. This is an ion exchange resin known as DEAE-Sephadex.

Chitin is a cellulose-like biopolymer consisting predominantly of unbranched chains of β-(1→4)-2-acetamido-2-deoxy-D-glucose (also named N-acetyl-D-glucosamine) residues. It is found in fungi, yeasts, marine invertebrates and arthropods, where it is a principal component in the exoskeletons. It may be regarded as a derivative of cellulose, in which the C-2 hydroxyl groups have been replaced by acetamido residues. Deacylated chitin, known as chitosan, is also useful.

Cellulose-based material used in chromatography or as ion exchange material, e.g., DEAE-cellulose (diethylaminoethyl cellulose) and ECTEOLA-cellulose, are also useful.

Pharmacologically-Active Agents Useful in the Invention

A "pharmacologically-active agent" includes any compound or composition of matter which, when administered to an organism (human or animal subject) induces a desired pharmacologic and/or physiologic effect by local and/or systemic action. The term therefore encompasses those compounds or chemicals traditionally regarded as drugs, biopharmaceuticals (including molecules such as peptides, proteins, nucleic acids), vaccines and gene therapies (e.g., gene constructs).

Pharmacologically-active agents useful in the composition of this invention include drugs acting at synaptic and neuroeffector junctional sites (cholinergic agonists, anticholinesterase agents, atropine, scopolamine, and related antimuscarinic drugs, catecholamines and sympathomimetic drugs, and adrenergic receptor antagonists); drugs acting on the central nervous systems; autacoids (drug therapy of inflammation); drugs affecting renal function and electrolyte metabolism; cardiovascular drugs; drugs affecting gastrointestinal function; chemotherapy of neoplastic diseases; drugs acting on the blood and the blood-forming organs; and hormones and hormone antagonists. Thus, the agents useful in the composition include, but are not limited to anti-infectives such as antibiotics and antiviral agents; analgesics and analgesic combinations; local and general anesthetics; anorexics; antiarthritics; antiasthmtic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, beta-blockers, beta-agonists and antiarythmics); antihypertensives; diuretics; vasodilators; central nervous system stimulants; cough and cold preparations; decongestants; diagnostics; hormones; bone growth stimulants and bone resorptioninhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like.

Specific examples of drugs useful in this invention include angiotensin converting enzyme (ACE) inhibitors, β-lactam antibiotics and γ-aminobutyric acid (GABA)-like compounds. Representative ACE inhibitors are discussed in Goodman and Gilman, Eighth Edition at pp. 757–762, which is incorporated herein by reference. These include quinapril, ramipril, captopril, benzepril, fosinopril, lisinopril, enalapril, and the like and the respective pharmaceutically acceptable salts thereof. Beta-lactam antibiotics are those characterized generally by the presence of a beta-lactam ring in the structure of the antibiotic substance and are discussed in Goodman and Gilman, Eighth Edition at pp. 1065 to 1097, which is incorporated herein by reference. These include penicillin and its derivatives such as amoxicillin and cephalosporins. GABA-like compounds may also be found in Goodman and Gilman. Other compounds include calcium channel blockers (e.g., verapamil, nifedipine, nicardipine, nimodipine and diltiazem); bronchodilators such as theophylline; appetite suppressants, such as phenylpropanolamine hydrochloride; antitussives, such as dextromethorphan and its hydrobromide, noscapine, carbetapentane citrate, and chlophedianol hydrochloride; antihistamines, such as terfenadine, phenidamine tartrate, pyrilamine maleate, doxylamine succinate, and phenyltoloxamine citrate; decongestants, such as phenylephrine hydrochloride, phenylpropanolamine hydrochloride, pseudoephedrine hydrochloride, chlorpheniramine hydrochlordie, pseudoephedrine hydrochloride, chlorpheniramine maleate, ephedrine, phenylephrine, chlorpheniramine, pyrilamine, phenylpropanolamine, dexchlorpheniramine, phenyltoxamine, phenindamine, oxymetazoline, methscopalamine, pseudoephedrine, brompheniramine, carbinoxamine and their pharmaceutically acceptable salts such as the hydrochloride, maleate, tannate and the like, β-adrenergic receptor antagonists (such as propanolol, nadalol, timolol, pindolol, labetalol, metoprolol, atenolol, esniolol, and acebutolol); narcotic analgesics such as morphine; central nervous system (CNS) stimulants such as methylphenidate hydrochloride; antipsychotics or psychotropics such as phenothiazines, trycyclic antidepressants and MAO inhibitors; benzadiazepines such as alprozolam, diazepam; and the like; and certain non steroidal antinflammatory drugs (NSAIDs), (e.g., salicylates, pyrazolons, indomethacin, sulindac, the fenamates, tolmetin, propionic acid derivatives) such as salicylic acid, aspirin, methyl salicylate, diflunisal, salsalate, phenylbutazone, indomethacin, oxyphenbutazone, apazone, mefenamic acid, meclofenamate sodium, ibuprofen, naproxen, naproxen sodium, fenoprofen, ketoprofen, flurbiprofen, piroxicam, diclofenac, etodolac, ketorolac, aceclofenac, nabumetone, and the like.

Another pharmacologically-active agent useful in the compositions and methods of this invention is an antigen, i.e., molecule which contains one or more epitopes that will stimulate a host's immune system to make a cellular antigen-specific immune response, or a humoral antibody response. Thus, antigens include proteins, polypeptides, antigenic protein fragments, oligosaccharides, polysaccharides, and the like. The antigen can be derived from any known virus, bacterium, parasite, plants, protozoans, or fungus, and can be a whole organism or immunogenic parts thereof, e.g., cell wall components. An antigen can also be derived from a tumor. An oligonucleotide or polynucleotide which expresses an antigen, such as in DNA immunization applications, is also included in the definition of antigen. Synthetic antigens are also included in the definition of antigen, for example, haptens, polyepitopes, flanking epitopes, and other recombinant or recombinant or synthetically derived antigens (Bergmann et al (1993) *Eur. J.*

*Immunol.* 23:2777–2781; Bergmann et al (1996) *J. Immunol.* 157:3242–3249; Suhrbier, A. (1997) *Immunol. And Cell Biol.* 75:402–408; Gardner et al (1998) 12$^{th}$ World AIDS Conference, Geneva, Switzerland (Jun. 28 –Jul. 3, 1998).

Thus when an antigen is associated with a hydrogel in accordance with the invention, it can be viewed as a "vaccine composition" and as such includes any pharmaceutical composition containing an antigen, which composition can be used to prevent or treat a disease or condition in a subject. The term encompasses both subunit vaccines, i.e., vaccine compositions containing antigens which are separate and discrete from a whole organism with which the antigen is associated in nature, as well as compositions containing whole killed, attenuated or inactivated bacteria, viruses, parasites or other microbes. The vaccine can also comprise a cytokine that may further improve the effectiveness of the vaccine.

Viral vaccine compositions used herein included, but are not limited to, those containing, or derived from, members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, meals virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1; and HIV-2); simian immunodeficiency virus (SIV) among others. Additionally, viral antigens may be derived from a papilloma virus (e.g., HPV); a herpes virus; a hepatitis virus, e.g., (HPV); a herpes virus; a hepatitis virus, e.g., hepatitis A virus (HAV), hepatitis B virus (HBV), hepatitis C virus (HCV), the delta hepatitis D virus (HDV), hepatitis E virus (HEV) AND hepatitis G virus (HGV) and the tick-borne encephalitis viruses. See e.g., Virology, 3$^{rd}$ Edition(W. K. Joklik ed. 1988); *Fundamental Virology*, 2$^{nd}$ Edition (B. N. Fields and D. M. Knipe, eds. 1991), for a description of these and other viruses. Bacterial vaccine compositions used herein include, but are not limited to, those containing or derived from organisms that cause diphtheria, cholera, tuberculosis, tetanus, pertussis, meningitis, and other pathogenic states, including Meningococcus A, B and C, Hemophilus influenza type B (HIB), and *Helicobacter pylori*. Examples of anti-parasitic vaccine compositions include those derived from organisms causing malaria and Lyme disease.

Suitable nucleotide sequences for use in the present invention include any therapeutically relevant nucleotide sequence. Thus, the present invention can be used to deliver one or more genes encoding a protein defective or missing from a target cell genome or one or more genes that encode a non-native protein having a desired biological or therapeutic effect (e.g., an antiviral function). The invention can also be used to deliver a nucleotide sequence capable of providing immunity, for example an immunogenic sequence that serves to elicit a humoral and/or cellular response in a subject, or a sequence that corresponds to a molecule having an antisense or ribozyme function.

Suitable genes which can be delivered include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemia and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. See, e.g., Han et al 1991) *Proc. Natl. Acad Sci. USA* 88:4313; Uhlmann et al (1990) *Chem. Rev.* 90:543; Helene et al (1990) *Biochim. Biophys. Acta.* 1049:99; Agarwal et al (1988) *Proc. Natl. Acad Sci. USA* 85:7079; and Heikkila et al (1987) *Nature* 328:445. A number of ribozymes suitable for use herein have also been described. See, e.g., Chec et al (1992) *J. Biol. Chem.* 267:17479 and U.S. Pat. No. 5,225,347 to Goldberg et al.

For example, in methods for the treatment of solid tumors, genes encoding toxic peptides (i.e., chemotherapeutic agents such as ricin, diphtheria toxin and cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, can be delivered for expression at or near the tumor site.

Similarly, genes coding for peptides known to display antiviral and/or antibacterial activity, or stimulate the host's immune system, can also be administered. Thus, genes encoding many of the various cytokines (or functional fragments thereof), such as the interleukins, interferons and colony stimulating factors, will find use with the instant invention. The gene sequences for a number of these substances are known.

For the treatment of genetic disorders, functional genes corresponding to genes known to be deficient in the particular disorder can be administered to the subject. The instant invention will also find use in antisense therapy, e.g., for the delivery of oligonucleotides able to hybridize to specific complementary sequences thereby inhibiting the transcription and/or translation of these sequences. Thus DNA or RNA coding for proteins necessary for the progress of a particular disease can be targeted, thereby disrupting the disease process. Antisense therapy, and numerous oligonucleotides which are capable of binding specifically and predictably to certain nucleic acid target sequences in order to inhibit or modulate the expression of disease-causing genes are known and readily available to the skilled practitioner. Uhlmann et al (1990) *Chem Rev.* 90:543, Neckers et al (1992) *Crit. Rev. Oncogenesis* 3:175; Simons et al (1992) *Nature* 359:67; Bayever et al (1992) *Antisense Res. Dev.* 2:109; Whitesell et al (1991) *Antisense Res. Dev.* 1:343; Cook et al (1991) *Anti-cancer Drug Design* 6:585; Eguchi et al (1991) *Annu. Rev. Biochem.* 60:631. Accordingly, antisense oligonucleotides capable of selectively binding to target sequences in host cells are provided herein for use in antisense therapeutics.

Other Composition Considerations

The compositions of the present invention are powders having hydrogel-containing particles of a size appropriate for high-velocity transdermal delivery to a subject, typically across the stratum corneum or a transmucosal membrane. The powder is generally flowable. The mean mass aerodynamic diameter of the particles forming the flowable powder can range from about 0.1 to 250 μm, preferably larger than about 20 μm, but smaller than about 100 μm, particularly less than 75 μm. More preferably, the majority of the particles will be in the range of about 40–60 μm. The particles of the powder generally have an envelope density of from 0.1 to 25 $g/cm^3$, preferably from 0.8 to 1.5 $g/cm^3$. While the shape of the individual particles may vary when viewed under a microscope, the shape is preferably approximately spheroidal, but may be elliptical, irregular in shape and/or toroidal. Hydrogels lend themselves to forming nearly spherical particles, which may have regular or irregular surfaces. Hydrogels also lend themselves to forming particles of a uniform density having the active agent associated with the hydrogel particle by absorption throughout the particle or simply by association with the hydrogel particle surface.

Because of the wide choice of hydrogels available, the amount of active agent present in a given composition can be easily varied depending on how much water a hydrogel may absorb. For example a highly soluble, highly active agent may be associated with a less absorptive hydrogel (because a lower concentration is needed), while a less active agent requiring a higher concentration should be associated with a more absorptive hydrogel. The active agent is thus present in the compositions of the present invention in amounts ranging from about 0.1 wt % to about 80 wt % and higher, although the active agent will typically be present in the instant compositions in an amount ranging from about 0.3 wt % to about 70 wt % such as from about 10 wt % to 60 wt % or from about 20 wt % to about $55$ wt %. The actual amount depends upon the activity of the agent, the dose desired, and other variables readily appreciated by the ordinarily skilled artisan upon reading the instant specification.

With the hydrogel compositions of the present invention, disassociation of the active agent from the hydrated hydrogel particles (e.g., hydrated upon delivery into living tissue) having a particle size ranging from about 10 to 100 μm is typically on the order of 0.1 to 1.0 seconds. With near instantaneous hydration of the hydrogel particle upon transdermal administration, release of the active agent is immediate for all practical purposes. This feature makes the present compositions particularly ideal for transdermal powder injection techniques requiring immediate delivery pharmacokinetics. However, in some embodiments, the chemical and/or physical water absorption and active dissolution rates can be altered to provide hydrogel compositions that feature sustained or delayed release capabilities.

Accordingly, in some compositions, hydrophilic or amphophilic agents are incorporated into the hydrogel compositions in order to slow the hydration rate of the dry particle and/or slow the rate of active release from the particle. Similar technologies can be used to coat the outside of the hydrogel particles in order to acheive a similar effect. For example, a lipophilic agent can be added to the internal and/or external areas of the hydrogel particle to reduce the direct exposure of the active agent to the absorbing water present in the target site, and also lowers the incidence of active degradation during processing (e.g., due to contact with processing solvents). Addition of such agents further slows the rate of water absorption into the particle, significantly slowing the rate of dissolution of the active from the hydrogel carrier. Since dissolution of the agent from a hydrosphere is a two step process (that of water absorption/ particulate hydration and expansion, followed by active dissolution and diffusion from the particle), there are dual opportunities to block or impede the route of active release.

Examples of hydrophobic agents capable of slowing the hydration and dissolution kinetics of the present hydrogel compositions are fatty acids and pharmaceutically acceptable salts thereof (e.g., magnesium stearate, steric acid, zinc stearate, palimitic acid, and sodium palitate). Other suitable agents include ampiphilic surfactants (glycerides, etc.) or polymers (e.g., polylactic glycolic acid (PLGA), polyortho esters). Starch components are also suitable for these purposes, as are semi-miscible solvents (i.e., solvents with partial miscibility in water) such as triacetin which can be added to the hydrogel particle to serve as a dissolution barrier. These solvents can further be employed to load hydrophobic agents into the hydrogel particle that otherwise would not carry into the hydrophilic environment of the hydrogel structure. In order to incorporate such agents into the hydrogel particles of the present invention, suitable methods can employ an organic or alcohol base solvent in which the hydrophobic agent is dissolved. Dry hydrogel particles (beads) can then be placed within the solvent in a ratio of solvent to particles that is at least sufficient to completely wet the particle surface. Additional solvent can then be used to build up thicker coatings. The final amount of hydrophobic agent absorbed into or onto the hydrogel particles depends upon the concentration of the coating agent in the solvent, the degree of swelling experienced by the hydrogel in the solvent, and the ratio of solvent to hydrogel.

In certain other embodiments, the hydrogel can be derivatived using standard chemistries to provide attractive sites within or on the particles and sufficient to associate a guest active agent (e.g., sites for ionic interaction with a guest agent). Alternatively, hydrogel polymer conjugates can be provided wherein the guest active agent is chemically bound (e.g., covalently bound) to the hydrogel to provide either altered release profiles (pharmacokinetics) or to associate particular agents with the hydrogel delivery platform. In this regard, numerous protein-polymer conjugate chemistries are known and well characterized in the art (see, e.g., Burnham, N. (1994) *Am. J. Hosp. Pharm.* 51:210–218) and are thus suitable for use with the compositions of the invention.

For the purposes of linking protein (and peptide) guest agents to the hydrogel (polymer) particles described herein, it is often preferred that the particular protein-polymer conjugate linkage be biodegradable in order to release the protein guest agent from the hydrogel in either a time-controlled fashion or in response to certain physiological conditions. One class of such biodegradable linkages are those wherein the chemical bond between the protein and polymer (hydrogel) is hydrolytically degraded. As will be appreciated by the ordinarily skilled artisan, upon reading the instant specification, common chemical linkages between proteins and polymers that are suitable for use herein include reactions with amino acid side chains (e.g., the ε-amino group of lysine and the α-amino groups of proteins (amide, thiourea, alkylamine and urethane linkages), the thiol group of free cysteine residues (thioether linkage), and carboxylic acid groups of aspartic and glutamic acid (amide and alkylamine). See, e.g., Duncan et al. (1994) *Adv. Polym. Sci.* 57:53–101 and Brinkley, M. (1992) *Bioconjugate Chem.* 3:2–13. Amide linkages generated with succinate estes (e.g., N-hydroxysuccinimide) are well known and have desirable hydrolytic instability (Lomants et al. (1976) *J. Mol. Biol* 104:243–248), and protein-polymer conjugates formed with succinate esters (e.g., succinimidyl succinate) are degradable under physiological conditions (Dreborg et al. (1990) *Crit. Rev. Ther. Drug Carrier Syst.* 6:315–365; Zalipsky et al. (1992) *Biotechnol. Appl. Biochem.* 15:100–114). In addition, thiol conjugation chemistries are degradable under physiological reducing conditions, providing reversible protein-polymer linkages (Woghiren et al. (1993) *Bioconjugate Chem.* 4:314–318) and enzymatically degradable linkages have been described wherein either proteins or pharmaceuticals are linked to polymer carriers via short peptide sequences (Kopecek et al. (1981) *Makromol. Chem.* 182:799–807).

The compositions of the invention may also include pharmaceutically acceptable excipients as a binder, carrier, stabilizer, glidant, antioxidant, pH adjuster, anti-irritant, and the like. Such an "excipient" generally refers to a substantially inert material that is nontoxic and does not interact with other components of the composition in a deleterious manner. The proportions in which a particular excipient may be present depend upon the purpose for which the excipient is provided and the identity of the excipient. Carriers such as dextran may be provided in any suitable amount such as from 10 to 75% by weight of the particles, for example from 20 to 70% or from 30 to 60% by weight.

Examples of suitable carriers that also act as stabilizers for peptides include pharmaceutical grades of dextrose, sucrose, lactose, trehalose, mannitol, sorbitol, inositol, dextran, and the like. The carrier may thus be a saccharide such as a monosaccharide, a disaccharide or a sugar alcohol. Other carriers include starch, cellulose, sodium or calcium phosphates, calcium sulfate, citric acid, tartaric acid, glycine, high molecular weight polyethylene glycols (PEG), and combinations thereof. It may also be useful to employ a charged lipid and/or detergent. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g. Brij, pharmaceutically acceptable fatty acid esters, e.g., lauryl sulfate and salts thereof (SDS), and like materials.

It may also be useful to use a penetration enhancer for the skin to assist in the delivery profile of particle compositions produced by the processes of the invention. A "penetration enhancer" or "permeation enhancer" as used herein relates to an increase in the permeability of skin to a pharmacologically active agent, i.e., so as to increase the rate at with the drug permeates through the skin and enters the bloodstream. The enhanced permeation effected through the use of such enhancers can be observed by measuring the rate of diffusion of an active agent through animal or human skin using a diffusion cell apparatus well known in the art. Penetration enhancers can be used to facilitate transdermal delivery characteristics, and to provide a desired therapeutic or prophylactic effect. An "effective" amount of a permeation enhancer as used herein means an amount that will provide the desired increase in skin permeability and, correspondingly, the desired depth of penetration, rate of administration, and amount of active delivered by the methods of the present invention.

Process of Preparation

Another aspect of this invention is a process for preparing a powdered composition suitable for transdermal administration to a subject using a high velocity particle injection technique. In broad terms, the process involves loading hydrogel particles with a pharmacologically-active agent. Hydrogel particles are formed which have the active agent associated therewith and which have suitable physical and functional characteristics for direct injection by a needleless syringe. The hydrogel particles may be preformed then have the active agent added to the particles, or the hydrogel material and the active agent can be combined to provide composition from which appropriate-sized particles may be formed in situ. In a preferred aspect, the process comprises:

providing a mixture of pre-formed hydrogel particles,
combining the particles with an aqueous composition containing (e.g., having dissolved and/or suspended therein) a pharmacologically active agent for a period sufficient to allow the agent to closely associate with the hydrogel particles and be incorporated therewith (e.g., the hydrogel may swell and incorporate the active agent therein), and
separating the hydrogel particles from the aqueous composition in a drying step (e.g., removing water and other solvents from the suspension using a suitable drying method) to obtain a powdered pharmaceutical composition. The powdered composition comprises substantially solid hydrogel particles having the active agent incorporated therewith, and is suitable for use in a transdermal powder injection device.

Preferably, each particle in the powder has a MMAD of about 10 to 100 µm. Any suitable drying method can be used, for example spray-drying, free-drying, spray-freeze drying, air-drying, vacuum-assisted drying and the like. However, freeze-drying and spray-drying are preferred methods. In one particular method, the preformed hydrogel particles are combined with the aqueous composition while still in a dry state. In another method, the pre-formed hydrogel particles are combined with the aqueous composition in a wet, pre-swollen state.

The process of preparing a hydrogel composition of this invention can be carried out by first forming hydrogel beads of the desired size, then associating the active agent therewith by combining the beads with an aqueous mixture of the active agent for a time sufficient for the active agent to associate with (e.g. be absorbed into and/or onto) the hydrogel beads. Approaches for preparing agarose beads are discussed herein above. These and other methods known to those of skill in the art can be used to prepare beads from other hydrogel materials. The beads, when dry can be comminuted to the desired particle size for the composition of this invention.

In another preferred aspect, the process comprises:
providing a mixture of pre-formed hydrogel particles,
suspending the hydrogel particles in an aqueous composition containing a pharmacologically active agent for a period sufficient to cause the particles to swell and incorporate the active agent therein, and
removing water and other solvents from the suspension in a drying step to obtain a powdered pharmaceutical composition. The powdered composition comprises the hydrogel particles that have the active agent incorporated therewith, and the method is carried out such that the mass mean aerodynamic diameter of the hydrogel particles in said powder composition is 10–100 µm. This can be readily managed by selection of a suitable size range for the pre-formed hydrogel particles.

In a still further preferred aspect, the process comprises;
providing a mixture of pre-formed hydrogel particles,
combining the particles with an aqueous composition containing (e.g. having dissolved and/or suspended therein) a pharmacologically active agent for a period sufficient to allow the agent to closely associate with the hydrogel particles and be incorporated therewith,
separating the hydrogel particles from the aqueous composition (e.g. removing water and other solvents from the particles) in at least a partial drying step to obtain primary loaded hydrogel particles having the active agent incorporated therewith,
combining the primary loaded hydrogel particles with the same or another aqueous composition containing the pharmacologically active agent for a period sufficient to allow further agent to closely associate with the hydrogel particles and be incorporated therewith, separating the hydrogel particles from the aqueous composition again using at least a partial drying process to obtain secondary loaded hydrogel particles having the active agent incorporated therewith. The secondary loaded particles can be treated in the same manner as the primary loaded particles in an iterative manner until either a desired active loading has been achieved in the hydrogel particles, or one reaches the highest practical active loading per particle on a dry weight basis. In any event, the final drying step is allowed to proceed to completion in order to provide particles that are suitable for transdermal delivery from a particle injection device. Here again, any suitable drying method can be used. For drying between iterative loading steps, partial drying (and preferably at least partial collapse of the particles) can be effected using a solvent such as acetone or an air-drying method. For the final drying step, freeze-drying and spray drying are again preferred.

In another preferred aspect, the process comprises:

forming an aqueous pharmaceutical formulation comprising a pharmacologically active agent and a hydrogel, the hydrogel being present at about 0.1 to 10 wt % of the formulation, and drying the formulation to obtain a powdered pharmaceutical composition comprising particles having a mass mean aerodynamic diameter of about 10–100 μm.

Under these methods of the present invention, particles suitable for delivery from a needleless syringe delivery device are produced by including a hydrogel in a particle formulation. The hydrogel is present in the final formulation at a level of about 0.1 to 95 wt %. The active agent is present in the final formulation at a level of about 0.1 to 85 wt %.

In those methods where the hydrogel monomers and guest substances are combined in a composition for subsequent in situ particle formation techniques, any of a number of conventional particle formation techniques can then be carried out to provide particles suitable for use in a particle injection technique, for example spray drying, extrusion cutting and drying (spherunization), fluid bed coating of seed particles, coacervation, collection and drying, wet granulation and milling, milling of solids or larger particles, precipitation of amorphous solids, fluid bed granulation, evaporation or air drying followed by milling, spray or melt cooling or prilling, spray freeze-drying, compression (i.e., pelleting and grinding), and the like.

Once formulated, the particles can be assessed using the following methods.

Particle Characterization Methods

Particle characterization for transdermal delivery from a needleless syringe (particle injection) has different requirements than for traditional pharmaceutical products. Most standard solid dosage forms place the highest value on facile dissolution. For example, in the preparation of tablets, density and particle size or morphology do not play an important role and individual particle density, an important parameter in determining momentum for particle injection, is typically not considered as long as flow characteristics are acceptable. However, for particulate compositions which are destined for direct injection, individual particle density is critical and thus multiple methods of characterization are typically used. Absolute and theoretical density determinations are made and correlated with delivery, efficiency. A number of methods are available such as pack density, either traditional light tap or instrumented techniques, envelope density and gradient flotation values. Other, indirect methods are available which correlate to density of individual particles. These include determination of surface area or void volumes, for example, using standard measures for BET and mercury intrusion densitometry.

Another key attribute for particles, particle size determination, is well known to be significantly influenced by methodology. The API Aerosizer® (Amherst Process Instruments, Hadley, Mass.) is a supersonic time-of-flight device in which the mode of measurement closely parallels the energetic helium jet basic to particle injection techniques. Data from this instrument, however, must be augmented with light microscopy including computer-aided image analysis techniques. Such information has also been compared to non-solvent suspension laser diffraction methodology, light obscuration techniques, and Coulter Counter® volume measurements. The latter techniques have been especially powerful to evaluate particles before and after passage through the transient high-energy acceleration jet used in transdermal particle injection delivery. As described below, metallized film or rigid foam targets give some quantitative information on the powder energy upon injection. Quantitative techniques which are directly related to the particle injection process are measurement of particle size distribution pre- vs. post-passage through a needleless syringe device and particle micro-hardness (i.e., impact strength when injected against a hard surface). Other techniques include direct particle indentation techniques (i.e., Nano Indenter II®, MTS Systems Corp, Oak Ridge, Tenn. or Micro Hardness Tester®, Anton Paar GmbH, Graz, Austria) in which a probe is used to measure the effect of force against a single particle on a light microscope stage.

Other tests of the properties of the hydrogel particle compositions described herein include in vitro skin penetration using full thickness human skin and Franz-type diffusion cells to measure delivery but also provide indication of drug dissolution and transport. A parallel to the metallized film energy test with a biological target is the use of trans-epidermal water loss (TEWL) measurements on skin in vitro after delivery. Particles are studied during formulation programs as well as pre- and post-delivery by light microscopy and scanning electron microscopy (SEM) to determine their initial morphology and/or changes during the transit of the highly energetic carrier gas flow.

Since dense particles are typically required for needleless syringe particle injection, particle formulation and/or drying conditions that can result in shrunk (or collapsed) particles are preferred. Ideally, excipients with Tg's (glass transition temperatures) lower than the primary drying temperature allow particles to collapse and result in dense particles. The use of a hydrogel which tends to collapse at certain water content or pH or temperature, and selection of suitable excipient components will significantly facilitate the production of dense particles that are suitable for these needleless syringe applications.

Treatment

In another aspect of the invention, a process is provided for delivering a pharmacologically active agent (drug, vaccine, diagnostic, etc.) to a subject in need thereof The process can broadly be described as a method for delivering a pharmacologically active agent to a subject using high-velocity, direct transdermal delivery, typically across a skin surface (e.g., through the stratum corneum) or into a mucosal membrane wherein the agent is associated with hydrogel particles of size appropriate for such high velocity delivery. More particularly, the process comprises preparing a pharmaceutical composition of matter comprising solid particles of about 0.1 to about 250 μm in average diameter, preferably about 10–100 μm in average diameter, wherein each particle comprises a hydrogel having associated therewith a pharmacologically active agent, accelerating said particles to a high velocity, and delivering said accelerated particles to a target surface present on a subject.

Another way of describing this aspect of the invention is to say it is a method of diagnosing, treating or preventing a condition in a subject by administering the compositions of the present invention via a needleless syringe to a subject in need of such treatment. As used herein, the term "treatment" or "treating" includes any of the following: the prevention of infection or reinfection; the reduction or elimination of symptoms; and the reduction or complete elimination of a pathogen. Treatment may be effected prophylactically (prior to infection) or therapeutically (following infection).

The compositions are delivered to the animal by high velocity delivery, preferably into skin or mucosal target sites, using the energy of a transient helium gas jet at a predetermined area of skin or mucosal tissue. A "predetermined area" is intended to be a defined area of intact unbroken living skin or mucosal tissue. That area will usually be in the range of about 0.3 cm$^2$ to about 10 cm$^2$. However, it will be appreciated by those skilled in the art of high-velocity particle delivery that the area of target tissue into which the composition is administered may vary significantly, depending on device configuration, dose, and the like. Injection velocities generally range from 100 to 3,000 m/sec such as from 200 to 2000 m/sec.

A detailed description of needleless syringe devices useful in the process of this invention is found in the prior art, as discussed herein. These devices are referred to as needleless syringe devices and representative of these devices are the dermal PowderJect® needleless syringe device and the oral PowderJect® needleless sringe device (PowderJect Technologies Limited, Oxford, UK). By using these devices, a therapeutically effective amount of the pharmacologicaly active agent is delivered to the subject. A therapeutically effective amount is that amount needed to give the desired pharmacologic effect. This amount will vary with the relative activity of the agent to be delivered and can be readily determined through clinical testing based on known activities of the compound being delivered. The "*Physicians Desk Reference*" and "*Goodman and Gilman's The Phamacological Basis of Therapeutics*" are useful for the purpose of determined the amount needed.

Needleless syringe devices for delivering particles were first described in commonly owned U.S. Pat. No. 5,630,796 to Bellhouse et al, incorporated herein by reference. Although a number of specific device configurations are now available, such devices are typically provided as a pen-shaped instrument containing, in linear order moving from top to bottom, a gas cylinder, a particle cassette or package, and a supersonic nozzle with an associated silencer medium. An appropriate powder (in the present case, a powder comprising the hydrogel particles) is provided within a suitable container, e.g., a cassette formed by two rupturable polymer membranes that are heat-sealed to a washer-shaped spacer to form a self-contained sealed unit. Membrane materials can be selected to achieve a specific mode of opening and burst pressure that dictate the conditions at which the supersonic flow is initiated. In operation, the device is actuated to release the compressed gas from the cylinder into an expansion chamber within the device. The released gas contacts the particle cassette and, when sufficient pressure is built up, suddenly breaches the cassette membranes sweeping the particles into the supersonic nozzle for subsequent delivery. The nozzle is designed to achieve a specific gas velocity and flow pattern to deliver a quantity of particles to a target surface of predefined area. The silencer is used to attenuate the noise produced by the membrane rupture.

A second needleless syringe device for delivering particles is described in commonly owned International Publication No. WO 96/20022. This delivery system also uses the energy of a compressed gas source to accelerate and deliver powdered compositions; however, it is distinguished from the system of U.S. Pat. No. 5,630,796 in its use of a shock wave instead of gas flow to accelerate the particles. More particularly, an instantaneous pressure rise provided by a shock wave generated behind a flexible dome strikes the back of the dome, causing a sudden eversion of the flexible dome in the direction of a target surface. This sudden eversion catapults a powdered composition (which is located on the outside of the dome) at a sufficient velocity, thus momentum, to penetrate target tissue, e.g., oral mucosal tissue. The powdered composition is released at the point of full dome eversion. The dome also serves to completely contain the high-pressure gas flow which therefore does not come into contact with the tissue. Because the gas is not released during this delivery operation, the system is inherently quiet. This design can be used in other enclosed or otherwise sensitive applications for example, to deliver particles to minimally invasive surgical sites.

In yet a further aspect of the invention, single unit dosages or multidose containers, in which the hydrogel particles of the invention may be packaged prior to use, can comprise a hermetically sealed container enclosing a suitable amount of the particles that make up a suitable dose. The particle compositions can be packaged as a sterile formulation, and the hermetically sealed container can thus be designed to preserve sterility of the formulation until use in the methods of the invention. If desired, the containers can be adapted for direct use in the above-referenced needleless syringe systems.

Powders of the present invention can thus be packaged in individual unit dosages for delivery via a needleless syringe. As used herein, a "unit dosage" intends a dosage receptacle containing a therapeutically effective amount of a powder of the invention. The dosage receptacle typically fits within a needleless syringe device to allow for transdermal delivery from the device. Such receptacles can be capsules, foil pouches, sachets, cassettes or the like.

The container in which the particles are packaged can further be labeled to identify the composition and provide relevant dosage information. In addition, the container can be labeled with a notice in the form prescribed by a governmental agency, for example the Food and Drug Administration, wherein the notice indicates approval by the agency under Federal law of the manufacture, use or sale of the hydrogel compositions contained therein for human administration.

Delivery of hydrogel particles from the above-referenced needleless syringe systems is practiced with particles having an approximate size generally ranging from 0.1 to 250 μm, preferably ranging from about 10–70 μm. Particles larger than about 250 μm can also be delivered from the devices, with the upper limitation being the point at which the size of the particles would cause untoward damage to cells at the target surface. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.1 and 25 g/cm$^3$, preferably between about 0.9 and 1.5 g/cm$^3$, and injection velocities generally range between about 100 and 3,000 m/sec. With appropriate gas pressure, particles having an average diameter of 10–70 μm can be accelerated through the nozzle at velocities approaching the supersonic speeds of a driving gas flow.

If desired, these needleless syringe systems can be provided in a preloaded condition containing a suitable dosage of the hydrogel particles described herein. The loaded syringe can be packaged in a hermetically sealed container, which may further be labeled as described above.

A number of novel test methods have been developed, or established test methods modified, in order to characterize performance of a needleless syringe device. These tests range from characterization of the powdered composition, assessment of the gas flow and particle acceleration, impact on artificial or biological targets, and measures of complete system performance. One, several or all of the following tests can thus be employed to assess the physical and functional suitability of the present hydrogel compositions for use in a needleless syringe system.

Assessment of Effect on Artificial Film Targets

A functional test that measures many aspects of powder injection systems simultaneously has been designated as the "metallized film" or "penetration energy" (PE) test. It is based upon the quantitative assessment of the damage that particles can do to a precision thin metal layer supported by a plastic film substrate. Damage correlates to the kinetic energy and certain other characteristics of the particles. The higher the response from the test (i.e., the higher the film damage/disruption) the more energy the device has imparted to the particles. Either electrical resistance change measurement or imaging densitometry, in reflectance or transmission mode, provide a reliable method to assess device or formulation performance in a controllable and reproducible test.

The film test-bed has been shown to be sensitive to particle delivery variations of all major device parameters including pressure, dose, particle size distribution and material, etc. and to be insensitive to the gas. Aluminum of about 350 Angstrom thickness on a 125 μm polyester support is currently used to test devices operated at up to 60 bar.

Assessment of Impact Effect on Engineering Foam Targets

Another means of assessing particle performance when delivered via a needleless syringe device is to gauge the effect of impact on a rigid polymethylimide foam (Rohacell 5 IIG, density 52 kg/m$^3$, Rohm Tech Inc., Malden, Mass.). The experimental set-up for this test is similar to that used in the metallized film test. The depth of penetration is measured using precision calipers. For each experiment a processed mannitol standard is run as comparison and all other parameters such as device pressure, particle size range, etc., are held constant. Data also show this method to be sensitive to differences in particle size and pressure. Processed mannitol standard as an excipient for drugs has been proven to deliver systemic concentrations in preclinical experiments, so the relative performance measure in the foam penetration test has a practical in vivo foundation. Promising powders can be expected to show equivalent or better penetration to mannitol for anticipation of adequate performance in preclinical or clinical studies. This simple, rapid test has value as a relative method of evaluation of powders and is not intended to be considered in isolation.

Particle Attrition Test

A further indicator of particle performance is to test the ability of various candidate compositions to withstand the forces associated with high-velocity particle injection techniques, that is, the forces from contacting particles at rest with a sudden, high velocity gas flow, the forces resulting from particle-to-particle impact as the powder travels through the needleless syringe, and the forces resulting from particle-to-device collisions also as the powder travels through the device. Accordingly, a simple particle attrition test has been devised which measures the change in particle size distribution between the initial composition, and the composition after having been delivered from a needleless syringe device.

The test is conducted by loading a particle composition into a needleless syringe as described above, and then discharging the device into a flask containing a carrier fluid in which the particular composition is not soluble (e.g., mineral oil, silicone oil, etc.). The carrier fluid is then collected, and particle size distribution in both the initial composition and the discharged composition is calculated using a suitable particle sizing apparatus, e.g., an AccuSizer® model 780 Optical Particle Sizer. Compositions that demonstrate less than about 50%, more preferably less than about 20% reduction in mass mean diameter (as determined by the AccuSizer apparatus) after device actuation are deemed suitable for use in the needleless syringe systems described herein.

Delivery to Human Skin in vitro and Transepidermal Water Loss

For a composition performance test that more closely parallels eventual practical use, candidate particle compositions can be injected into dermatomed, full thickness human abdomen skin samples. Replicate skin samples after injection can be placed on modified Franz diffusion cells containing 32° C. water, physiologic saline or buffer. Additives such as surfactants may be used to prevent binding to diffusion cell components. Two kinds of measurements can be made to assess performance of the formulation in the skin.

To measure physical effects, i.e. the effect of particle injection on the barrier function of skin, the transepidermal water loss (TEWL) can be measured. Measurement is performed at equilibrium (about 1 hour) using a Tewameter TM 210® (Courage & Khazaka, Koln, Ger) placed on the top of the diffusion cell cap that acts like a ~12 mm chimney. Larger particles and higher injection pressures generate proportionally higher TEWL values in vitro and this has been shown to correlate with results in vivo. Upon particle injection in vitro TEWL values increased from about 7 to about 27 ($g/m^2h$) depending on particle size and helium gas pressure. Helium injection without powder has no effect. In vivo, the skin barrier properties return rapidly to normal as indicated by the TEWL returning to pretreatment values in about 1 hour for most powder sizes. For the largest particles, 53–75 μm, skin samples show 50% recovery in an hour and full recovery by 24 hours.

Delivery to Human Skin in vitro and Drug Diffusion Rate

To measure the formulation performance in vitro, the active (guest) component(s) of candidate compositions can be collected by complete or aliquot replacement of the Franz cell receiver solution at predetermined time intervals for chemical assay using HPLC or other suitable analytical technique. Concentration data can be used to generate a delivery profile and calculate a steady state permeation rate. This technique can be used to screen formulations for early indication of drug binding to skin, drug dissolution, efficiency of particle penetration of stratum corneum, etc., prior to in vivo studies.

These and other qualatative and quantitative tests can be used to assess the physical and functional suitability of the present hydrogel particle compositions for use in a high-velocity particle injection device. It is preferred, though not required, that the hydrogel compositions have the following characteristics; a substantially spherical shape (e.g., an aspect ratio as close as possible to 1); a smooth surface; have a high active loading content (e.g., up to 80 or 90% loading); less than 20% reduction in particle size using the particle attrition test; an envelope density as close as possible to the true density of the constituents (e.g., greater than about 0.8 g/ml); and a MMAD of about 20 to 50 µm with a narrow particle size distribution. The compositions may be free flowing (e.g., free flowing after 8 hours storage at 50% relative humidity and after 24 hours storage at 40% relative humidity). All of these criteria can be assessed using the above-described methods, and are further detailed in the following publications, incorporated herein by reference. Etzler et al (1995) *Part. Part. Syst. Charact.* 12:217; Ghadiri, et al (1992) *IFPRI Final Report, FRR* 16–03 *University of Surrey, UK;* Bellhouse et al (1997) "Needleless delivery of drugs in dry powder form, using shock waves and supersonic gas flow," Plenary Lecture 6, 21st *International Symposium on Shock Waves, Australia;* and Kwon et al (1998) *Pharm. Sci.* suppl.1 (1), 103.

The following examples are provided to further explain the details of this invention but are not meant to limit the scope of the invention in any way.

C. Experimental

Below are examples of specific embodiments for carrying out the methods of the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

The objective of this example is to evaluate the performance of insulin delivery following the administration of insulin-loaded, powdered agarose bead compositions of this invention and to compare insulin relative bioavailability (to subcutaneous injection) following administration of standard lyophilised and agarose bead insulin powdered formulations via high velocity transdermal delivery to mice. The overall approach was to administer a 1 mg dose of powdered insulin formulation to an anaesthetised rat (n=4–6 rats for each formulation) using a dermal PowderJect® needleless syringe device (PowderJect Technologies, Limited, Oxford, UK). Two agarose bead compositions of this invention were compared to a standard lyophilised insulin powder formulation. Arterial blood samples were collected periodically following administration of each dose, and insulin and glucose concentrations were determined. Insulin pharmacokinetics and glucose dynamics following transdermal particle injection administration were compared to those observed following subcutaneous injection.

A single phase 1 clinical PowderJect needleless syringe fitted with a porous silencer sleeve, 12° conical nozzle (with an 11.7 mm exit bore), 5 ml gas canister and 0.5 ml rupture chamber was used throughout the entire study. Gas driver pressure was kept constant at 60 bar.

I. Insulin Formulations

Powdered agarose bead and standard lyophilised insulin formulations were administered via a needleless syringe device. Insulin solutions were freshly prepared for subcutaneous injection.

A. Standard Lyophilised Formulations

Lyophilised powdered formulations containing 0 and 100 μg human insulin (26.9 U/mg, Diosynth BV, 5340 BH Oss, Netherlands) per mg in a mixture of mono- and di-sodium hydrogen phosphate (theoretical pH 7.7, ) as the bulking excipient, were processed follows: the powder was compressed using a carver press into 3 discs, 0.3–0.4 g each, at 15,000 lbs./sq. inch for 45 seconds. The discs were then ground in a pestle and mortar to give a fine white powder. Approximately 1 g of the powder was sieved (Fritsch Analysette 28 sonic sieve) using three mesh sizes, 38 μm, 53 μm and 75 μm. The sieving program was 0–40% amplitude over 4 minutes, 40% amplitude for 5 minutes, and 40–0% amplitude over one minute (total run time 10 minutes). The sieve fractions were dispensed into airtight polypropylene (Nalgene®) bottles and stored at 2–8° C.

B. Agarose Bead Compositions of this Invention

Powdered agarose bead formulations were produced using porcine insulin (25.6 U/mg, Diosynth BV, 5340 BH Oss, Netherlands) provided by PowderJect Technologies Limited. Two formulations were included in this study, both containing a nominal insulin content of approximately 100 μg porcine insulin per mg (Table 1). In each case, the formulations were prepared by hydrating dry beads in a 100 μg/ml insulin solution and drying the beads thus loaded with insulin.

TABLE 1

Agarose bead insulin formulations evaluated in this study

| Batch No. | Nominal content (w/w) |
|---|---|
| CG 0904 | Porcine insulin 13%, dextran 63%, agarose 24% |
| CG 0920 | Porcine insulin 10%, agarose 90% |

C. Insulin Solutions for Subcutaneous Administration 10 mg of a 1% w/w (nominal) powdered insulin in phosphate buffer powdered formulation was weighed into a 2 ml glass standard flask. The flask was made up to volume with normal saline with gentle mixing until complete dissolution on the day of administration. The dose volume of 0.2 ml contained a nominal 10 μg dose of insulin.

II. Preparation of the Drug Cassettes

The powdered formulations (sections IA and IB) were accurately weighed out on a 5 decimal-place balance, and dispensed as 1 mg (±10%), payloads into 7-piece research drug cassettes (Plasro 2) containing 20 μm polycarbonate membranes. The actual tare mass of payload was recorded for each cassette. Cassettes were then stored at 2–8° C. and protected from physical movement until usage. Drug-filled cassettes were allowed to reach room temperature prior to firing.

III. Test Animal Preparation and Dosing

Sprague Dawley rats (Charles River) weighing 300 g±10% were anaesthetised by a 1 ml IP injection of freshly prepared FFM mixture (Hypnovel®, Hypnorm® and WFI, 1:1:2 by volume). An area of skin (approx. 9 $cm^2$) was closely shaved by clippers and a high quality disposable razor on the rat's lower right abdomen 1 cm from the midline. The site was rinsed and dabbed dry with cotton swabs. The right carotid artery was surgically isolated and cannulated with polyethylene tubing. The cannula was connected to a syringe filled with heparinised saline (10 U/mi) via a 3 way tap.

Anaesthesia was maintained by i.p. injections of FFM mixture, 0.5 ml every 45 min or as required. Rectal temperature was maintained between 35–38° C. for the duration of the experiment using a K-Temp® rectal probe and thermostat-controlled heating pad.

Rats were allowed to equilibrate for at least 15 minutes following surgery, prior to administration of the dose.

A. Subcutaneous Dose

The dose (0.2 ml, section IC) was administered to the anaesthetised rat under a skin fold of the lower left abdomen via a 1 ml syringe fitted with a 26 G needle. Six rats received the subcutaneous dose.

B. Dermal Particle Injection (PJ) Dose

A drug cassette (section IB) was loaded into the phase 1 clinical needleless syringe (PowderJect device, Section 1.1). The loaded device was then immediately actuated onto the shaved section of the rat's abdomen using a consistent procedure. Each formulation was evaluated in four or five rats.

IV. Blood Sampling

Blood samples (0.4 ml) were collected via the arterial cannula into 1 ml disposable syringes prior to and 10, 20, 40, 60, 120, and 240 minutes following the dose. 0.25 ml of saline (and some blood) was withdrawn into a separate syringe prior to each sample, and this volume was immediately returned to the rat to minimise the reduction in blood volume during the experiment.

The blood sample was immediately transferred into a heparinised 1.5 ml polypropylene centrifuge tube and centrifuged (2 min, 9000 rpm) in a microcentrifuge. The plasma decanted and stored at 2–8° C. for subsequent analysis within 7 days of collection.

V. Analysis of Plasma Samples

Each sample was analysed for insulin concentration by a radioimmunoassay kit (Coat-a-Count®, DPC, Los Angeles, Calif. 90045). The kit was used in accordance with the manufacturer's instructions, with the following modifications:

Standards (0.1, 0.3, 1, 3, 10, 20, 40, and 80 ng/ml) were freshly prepared by spiking blank, de-insulinised rat plasma with stock solutions of the same insulin (porcine or human) used to prepare the formulations (section 1.2).

The incubation period was performed at 2–8° C. to inhibit radiolysis catalysed by a component of rat serum.

Under these conditions, the coefficients of variation at 0.3, 5, and 40 ng/ml were 12%, 4%, and 8% respectively. No degradation was detected in control samples stored at 2–8° C. for up to one week.

VI. Analysis of Insulin Formulations

A. Insulin Content

Powdered insulin formulations were accurately reconstituted in a stabilising buffer (Tween 20 0.002%, thiomersal 0.25 mg/ml, and tetrasodium EDTA 0.1 mg/ml in phosphate buffer pH 8.0) to nominal insulin concentrations in the range 0.1–1 mg/ml. These solutions were immediately transferred to glass HPLC autosampler vials and stored at 6° C. until analysis, not more that 72 h later.

Analyses were performed on a Hewlett Packard 1100 HPLC system fitted with a Genesis cartridge column (15 em, C18, 4 gm, 300 Å), according to methodology previously described (L. J. Janis et al 1996). The insulin peak was well resolved from its principal degradation and aggregation products.

Samples insulin concentrations were calculated by peak area against standard curves constructed from freshly prepared standard solutions of insulin (same batches as those used for the formulations) over the range 0.1–1 mg/ml. Standard curves were linear ($r^2 > 0.999$) and previous work had shown that under these conditions, at a nominal concentration of 1.5 μg/ml, the coefficient of variation and accuracy were 1.7% and 2.3% respectively.

The assayed content of each powdered formulation was expressed as μg/mg insulin.

B. Particle Size Range Analysis

Samples of each powdered formulation were submitted for particle size range distribution analysis using an Amherst Process Instruments Aerosizer LD fitted with Dry Powder Dispersion System, according to standard procedures. The volume distribution data were analysed by geometric diameter.

VII. Pharmacokinetic Analysis

Net plasma insulin concentrations following administration of the dose were calculated by subtracting the apparent concentration in the pre-dose sample (t=0) from the raw concentration measured at each time point.

A. Calculation of the Dose ($X_0$)

The dose of insulin administered via DPJ was calculated for each rat as the assayed insulin content of the powdered formulation (μg/mg) multiplied by the mass of formulation weighed into the individual cassette (mg).

The dose of insulin administered subcutaneously was calculated for each rat as the assayed insulin content of the powdered insulin formulation (section IC) (μg/mg) multiplied by the mass of powder weighed out (mg), divided by the volume of reconstitution (ml) and then multiplied by 0.2 ml (the volume administered by injection).

For the purposes of pharmacokinetic calculations, the dose was expressed as μg/kg body weight.

B. Calculation of the Area Under the Plasma Insulin Conc. vs Time Curve (AUC)

The net AUC for each rat was calculated from the net plasma insulin concentration vs time profile by trapezoidal rule from 0 to 240 minutes.

C. Calculation of Relative Bioavailability

The bioavailability ($BA_{rel}$) of insulin delivery via DPJ relative to subcutaneous administration ($BA_{rel}$) was calculated by the standard equation:

$$BA_{rel} = \frac{Net\ AUC_{DPJ} / Xo_{DPJ}}{Net\ AUC_{sc} / Xo_{sc}}$$

VIII. Results

The relevant pharmaceutical characteristics of each formulation are presented in Table 2. It is noteworthy that the assayed insulin content varied by as much as 24% (CG 0904) from the nominal insulin content, resulting in doses via DPJ ranging from 287 to 421 μg of insulin per kg.

TABLE 2

| Formulation | Nominal insulin content (μg/mg) | Assayed insulin content (μg/mg) | Mean $X_0$ (μg/kg) | $D_p$ (μm) | $D_{10}^-$ $D_{90}$ (μm) | ?? Fines (<25 μm) |
|---|---|---|---|---|---|---|
| Subcutaneous dose Standard lyophilised: | NA | 8.7* | 28.3 | NA | NA | NA |
| Placebo | 0 | 0 | 0 | NA | NA | NA |
| Insulin 10% w/w | 100 | 88.3 | 287 | 41 | 30–57 | 3.3 |

TABLE 2-continued

| Formulation | Nominal insulin content (μg/mg) | Assayed insulin content (μg/mg) | Mean $X_0$ (μg/kg) | Particle size analysis $D_p$ (μm) | $D_{10}$– $D_{90}$ (μm) | ?? Fines (<25 μm) |
|---|---|---|---|---|---|---|
| Agarose bead: | | | | | | |
| CG 0904 | 130 | 99 | 353 | 55 | 44–68 | 0.3 |
| CG 0920 | 100 | 122 | 421 | 44 | 30–62 | 3.6 |

*-assayed insulin content of powder reconstituted for SC dose
NA-not applicable

The raw radioimmunoassay and plasma concentration data for each rat are not presented here. Mean net plasma insulin concentration vs time profiles following administration of the four powdered formulations by DPJ, compared to subcutaneous administration, are presented in FIG. 1. In the group of rats that received the placebo dose, the apparent background plasma insulin concentration remained constant over the sampling period. This data served as an indicator of physiological stability over the duration of the experiment in the anaesthetised rat model. The mean time taken to reach maximal plasma concentration ($T_{max}$) ranged from 10 to 30 minutes for all DPJ and subcutaneous groups (Table 3).

The mean maximal plasma insulin concentration ($C_{max}$) following administration of the standard lyophilised powder formulation was 9.3 ng/ml, which compared to 14 ng/ml for agarose formulation CG 0920 (insulin/agarose), and 26 ng/ml for agarose formulation CG 0904 (insulin/dextran/agarose). In all of the experimental groups, plasma insulin concentrations returned to baseline levels by 4 hours.

Net AUC data and the calculated mean relative bioavailabilities ($BA_{rel}$) of insulin administered via DPJ are presented in Table 3. The standard lyophilised powder formulation yielded a $BA_{rel}$ of 15.6%. Despite a higher $C_{max}$, no improvement in insulin delivery was seen with agarose formulation CG 0920 (insulin/agarose). However, for agarose formulation CG0904 (insulin/dextran/agarose), $BA_{rel}$ was 34%, more than double that observed with the standard powdered formulation. With this formulation, the inter-animal variability, measured by the coefficient of variation (CV), was comparable to that observed following subcutaneous administration (19% vs 24% respectively).

TABLE 3

Pharmacokinetic parameters of insulin delivered via DPJ (standard and agarose bead formulations) compared to subcutaneous administration.

| Formulation/route | $X_0$ (μg/kg) | $T_{max}$ (min) | $C_{max}$ (ng/ml) | net AUC (ng.min/ml) | $BA_{rel}$ (CV, %) |
|---|---|---|---|---|---|
| Subcutaneous (n = 6) | 28.3 ± 2.7 | 10 ± 0 | 4.56 ± 1.69 | 42.5 ± 102 | 100% (24) |
| Standard (DPJ, n = 6) | 287 ± 17 | 30 ± 0 | 9.28 ± 1.90 | 674 ± 226 | 15.6% (34) |
| CG 0904 (DPJ, n = 5) | 353 ± 13 | 22 ± 11 | 25.8 ± 4.8 | 1800 ± 341 | 34.0% (19) |
| CG 0920 (DPJ, n = 5) | 429 ± 35 | 18 ± 4 | 14.0 ± 10.3 | 675 ± 338 | 10.5% (50) |

All data expressed as mean ± SD

The agarose bead formulations of this invention are shown to be effective in delivering insulin into the systemic circulation. Absorption was expected to be prolonged in agarose formulation CG 0920, because agarose is insoluble in water and accounted for approximately 90% of the formulation by weight. This was not shown to be the case, although the lower $BA_{rel}$ and greater variability of the plasma insulin profiles observed may suggest that the release of the insulin payload was variable and not as efficient once this formulation was administered into the skin The marked improvement in insulin delivery associated with the agarose formulation CG 0904 was initially thought to be attributable to greater particle size. Thus it was originally thought that particle size correlated with increased BA. It has now been determined that addition of dextran to the beads prevents collapse during drying and thus improves particle performance.

EXAMPLE 2

This example sets forth a composition of this invention and a process for its preparation. The particular active (guest agent) was lactate dehydrogenose (LDH) and the hydrogel was agarose (Bio-Gel A15M).

Lactate dehydrogenase (LDH) was obtained from Sigma Chemicals (L1254; Lot 96H9568). Bio-Gel A15M was obtained from Bio-Rad (Cat. No. 151–1050) as a powder having a MMAD of 20–150 μm. LDH activity was measured using an endpoint, colorimetric assay (Sigma No. 500). All other reagents were obtained from Fisher Scientific and were ACS-grade or better.

The Bio-Gel A15M resin was washed with water to remove preservative and then poured into a disposable 1×10 cm column to a final column volume of approximately 5 mL. The column was equilibrated with 5 mL sodium citrate, pH 6 containing 5% (w/v) mannitol. LDH was dissolved in the same buffer at 2 mg/mL final concentration. A 5 mL sample of this solution was loaded to the column and allowed to fully penetrate.

The resin was emptied from the column and lyophilized. After lyophilization the resin was re-suspended in water and poured back into the column. The column was then eluted with a 5 mL portion of the buffer. A sample of the original LDH solution was also lyophilized and then redissolved to the original volume with water.

The protein concentration of each solution was determined by absorbance at 280 nm using a Hewlett-Packard UV-VIS Spectrophotometer. The LDH activity assay is based on the conversion of pyruvic acid to lactic acid in the presence of NADH. The remaining pyruvic acid is treated with 1,4-dinitrophenylhydrazine to give a highly colored product. The absorbance of the color formed is inversely proportional to the LDH activity. LDH specific activity was calculated by dividing the absorbance at 280 nm ("protein concentration") by the absorbance at 442 nm ("enzymatic activity").

The LDH recovered after lyophilization from solution had a specific activity which was 98% of the starting material. The material which was eluted from the agarose beads showed a specific activity of about 40% of the starting material. This was a preliminary study and the assay technique was not optimized. The samples measured were all very high in LDH activity and were at the top end of the standard curve. Essentially this shows that an enzyme can be loaded onto an agarose bead, lyophilized and recovered with activity.

EXAMPLE 3

Two calcitonin formulations: calcitonin/trehalose/mannitol (8/52/mannitol, q.s.a.d.)±3% of poly(N-isopropylacrylamide) are used as the model hydrogel with the total solid concentration at 20%. The liquid formulation (10 mL) is atomized using an ultrasonic atomizing system (frequency at 60 kHz) into a tray of liquid nitrogen. The resulting ice droplets/liquid nitrogen mixture is placed in a freeze dryer pre-chilled at −50° C. The dryer is warmed to −25° C. in 1 hour and maintained at −25° C. for one hour with a vacuum pulled at minimum 0.1 mbar. The primary drying is then continued at a ramping temperature profile (increasing from −25° C. to 0° C. over 30 hours). At the end of the primary drying, the temperature is increased to 20° C. in an hour and maintained at 20° C. for another 12 hours for the secondary drying. After drying, a volume comparison of the two powder formulations at the same sample weight shows that the hydrogel-containing formulation has less volume, indicating higher particle density.

EXAMPLE 4

In order to assess the ability to load a guest agent into dextran beads (serving as the hydrogel carrier particle in the compositions of the present invention) and to then extract the loaded agent from the hydrogel in an aqueous environment, the following study was carried out.

Dextran beads, sulfated, 4% w/v cross-linked, were obtained from Sigma (Sigma, St. Louis Mo., Catalogue No. D-5650, Lot No. 111H9575). Insulin was obtained from Akzo Nobel (SIPP584)vLysozyme. The insulin was dissolved in 1.5% acetic acid solution to provide a loading solution. The concentration of the loading solution was 10.10 mg/ml. 4.199 g of the loading solution was added to 4.155 g of hydrated dextran beads. The resulting suspension was mixed and allowed to equilibrate for 1 hr at room temperature. After this loading process, the beads were separated from the loading solution, and the loading solution analyzed for protein concentration. The beads were subsequently freeze-dried.

The dried, loaded beads were then added to an aqueous extraction solution, and the extraction solution was analyzed for protein concentration.

Insulin concentrations from both the initial and remaining loading solution, as well as from the extraction solution were determined using a BioRad (Richmond, Calif.) UV detector. A standard curve (UV absorption vs. insulin concentration) was prepared by measuring the UV absorption of insulin solution at different concentrations, ranging from 4.41 mg/ml to 10.10 mg/ml. Insulin concentrations of the various solutions were then determined by extrapolation of the standard curve.

As a result of the study, the initial loading solution was found to contain 42.4 mg of insulin, while 3.2 mg remained in the loading solution after the 1 hour equilibration with the dextran beads. Percent loading of insulin was thus calculated at 25% upon lyophilization of the loading beads, resulting in a loading efficiency of 92%. The extraction solution was found to have 31 mg of insulin, providing a percent recovery of 79% from the loaded dextran beads.

EXAMPLE 5

In order to demonstrate the ability of the multiple-loading method of the present invention to incorporate additional protein guest agent in hydrogel carrier particles, the following study was carried out.

4% agarose beads (XC Corporation, Lot # XB219) and 8% agarose beads (XC Corporation, Lot # XB138) were obtained for use as the hydrogel carrier system. Porcine insulin (Akzo Nob (XC Corporation, Lot # XB219)el, Lot SIPP 584) was used as the guest agent. The agarose beads were lyophilized (using a VirTis Sentry™ Model 3+ES freeze drying apparatus) overnight to obtain dried agarose beads. The dried beads were then rehydrated by combining the same with saturated porcine insulin solution (25 mg/ml in 1% acetic acid solution) and allowing the suspension to equilibrate. The loaded particles were then separated from the loading solution, and lyophilized for 48 hours to dry the loaded (rehydrated) beads. This procedure resulted in the primary loading. The above technique was then repeated using dried primary beads to result in a secondary loading (loading #2). Dried secondary beads were then added to the loading solution in the same manner, and this procedure repeated to provide secondary loading numbers #3 to #5. Beads from each loading iteration were then placed into an extraction solution, and the insulin content from each of the primary (#1) and secondary loadings (#2 to #5) was then determined using Reverse Phase HPLC (Shimadzu VP HPLC). Untreated beads (Loading #0) were also analyzed by HPLC to provide a negative loading control.

Figure 2:
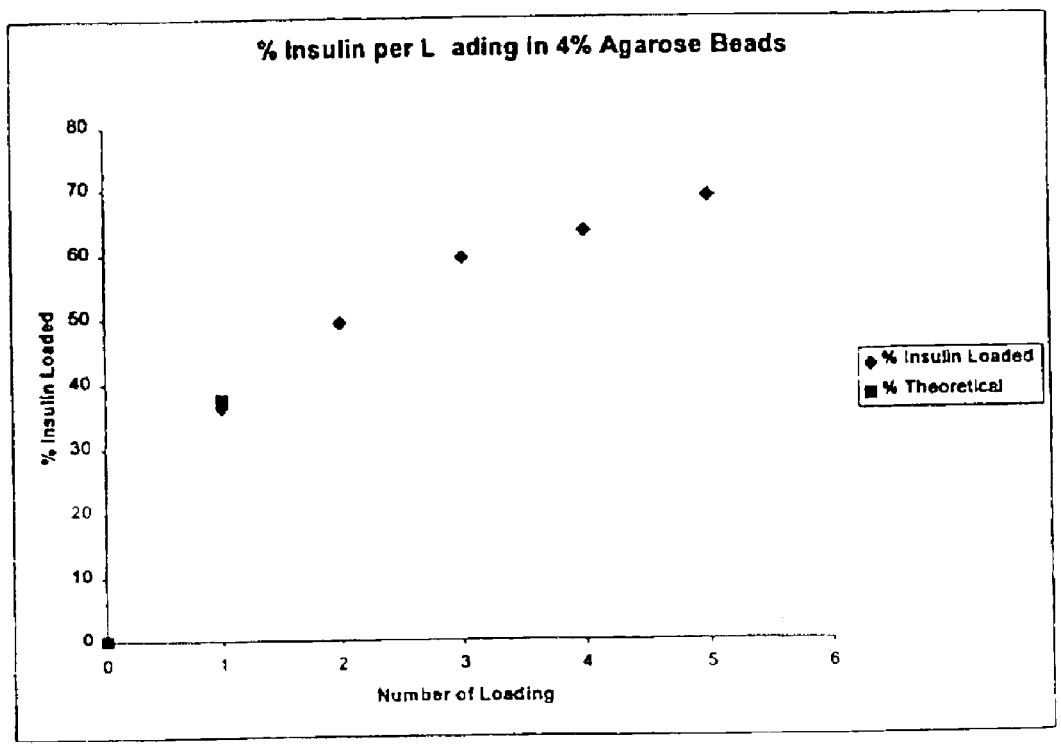
FIGS. 2 and 3 show the percentage of insulin loaded (♦) in Example 5 in 4% agarose beads and 8% agarose beads respectively. The percentage theoretically loaded (■) is also shown.
Figure 3:
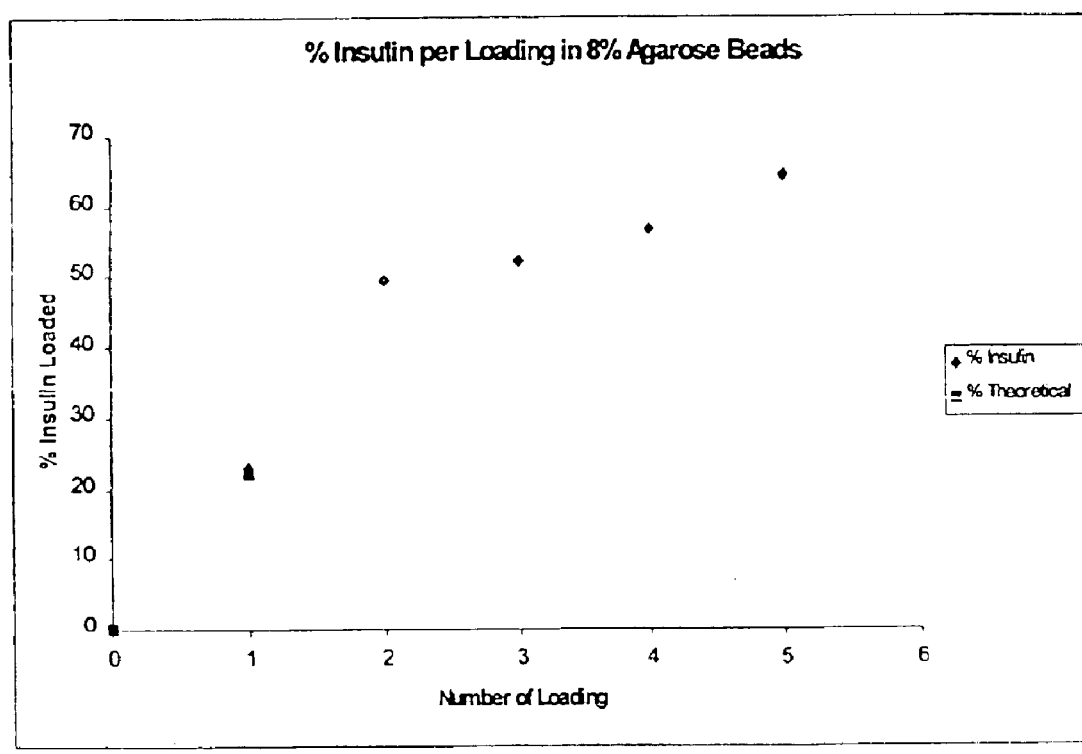

The results of the study for the 4% beads are presented below in Table 4 below and in FIG. 2. The results of the study for the 8% beads are presented below in Table 5 below and in FIG. 3. The maximum % insulin loading by theoretical calculation in a single loading step is 37.5% for the 4% agarose beads, and 22.3% for the 8% agarose beads.

TABLE 4

| Loading # | % Insulin Loaded | Std. Dev. | % CV |
| --- | --- | --- | --- |
| 0 | 0 | 0 | 0 |
| 1 | 36.32 | 0.2 | 0.5 |
| 2 | 49.24 | 1.2 | 2.4 |
| 3 | 59.15 | 0.6 | 1.1 |
| 4 | 63.28 | 2.4 | 3.8 |
| 5 | 68.65 | 0.6 | 0.9 |

TABLE 5

| Loading # | % Insulin Loaded | Std. Dev. | % CV |
| --- | --- | --- | --- |
| 0 | 0 | 0 | 0 |
| 1 | 23.08 | 0.1 | 0.5 |
| 2 | 49.65 | 0.3 | 0.7 |
| 3 | 52.08 | 0.7 | 1.3 |
| 4 | 56.61 | 0.4 | 0.6 |
| 5 | 64.42 | 1.1 | 1.7 |

As can be seen by these results, the multiple (iterative) loading method of the present invention is suitable to provide for extremely high drug loading per particle on a dry weight basis.

All publications and patent applications mentioned in this specification are herein incorporated by reference to the same extent as if each individual publication or patent application was specifically and individually indicated to be incorporated by reference.

The invention now being fully described, it will be apparent to one or ordinary skill in the art that many changes and modifications can be made thereto without departing from the spirit or scope of the appended.

What is claimed is:

1. A method for making a powdered pharmaceutical composition, said method comprising:
   (a) providing a mixture of pre-formed hydrogel particles;
   (b) contacting the hydrogel particles with an aqueous composition containing at least one pharmacologically active agent for a period sufficient to allow the agent to associate with the hydrogel particles and be incorporated therewith;
   (c) separating the hydrogel particles from the aqueous composition in at least a partial drying step to obtain primary loaded hydrogel particles having the active agent incorporated therewith;
   (d) contacting the primary loaded hydrogel particles with an aqueous composition containing said pharmacologically active agent for a period sufficient to allow further agent to associate with the hydrogel particles and be incorporated therewith;
   (e) separating the hydrogel particles formed in step (d) from the aqueous composition in at least a partial drying step to obtain secondary loaded hydrogel particles having the active agent incorporated therewith; and
   (f) drying the secondary loaded hydrogel particles to obtain a powdered pharmaceutical composition.

2. The method of claim 1, wherein prior to step (f), the secondary loaded hydrogel particles formed in step (e) are contacted at least one further time with an aqueous composition containing said pharmacologically active agent for a period sufficient to allow still further agent to associate with the hydrogel particles and be incorporated therewith.

3. The method of claim 1, wherein the hydrogel particles in step (b) are contacted with the aqueous composition while in a dry state.

4. The method of claim 1, wherein the hydrogel particles in step (b) are contacted with the aqueous composition while in a wet, prehydrated state.

5. The method of claim 1, wherein the hydrogel particles comprise agarose, dextran, cellulose, chitin, starch, polyvinylpyrrolidone or polyvinyl alcohol.

6. The method of claim 1, wherein the active agent is present in the powdered pharmaceutical composition in an amount ranging from about 0.1 to 85 wt % of the composition.

7. The method of claim 1, wherein the powdered pharmaceutical composition is formed using a freeze-drying step.

8. The method of claim 1, wherein the powdered pharmaceutical composition is formed using a spray-drying step.

9. A method for making a powdered pharmaceutical composition, said method comprising:
   (a) providing a mixture of pre-formed hydrogel particles;
   (b) contacting the hydrogel particles with an aqueous composition containing at least one pharmacologically active agent for a period sufficient to allow the agent to associate with the hydrogel particles and be incorporated therewith;
   (c) separating the hydrogel particles from the aqueous composition in at least a partial drying step to obtain primary loaded hydrogel particles having the active agent incorporated therewith;
   (d) contacting the primary loaded hydrogel particles formed in step (c) at least one further time with an aqueous composition containing said pharmacologically active agent for a period sufficient to allow further agent to associate with the bydrogel particles and be incorporated therewith arid separating the hydrogel particles formed from the aqueous composition at least one further time in at least a partial diying step to obtain loaded hydrogel particles having the active agent incorporated therewith; and
   (e) drying the loaded hydrogel particles to obtain a powdered pharmaceutical composition.

10. The method of claim 9, wherein the hydrogel particles in step (b) are contacted with the aqueous composition while in a dry state.

11. The method of claim 9, wherein the hydrogel particles in step (b) are contacted with the aqueous composition while in a wet, prehydrated state.

12. The method of claim 9, wherein the hydrogel particles comprise agarose, dextran, cellulose, chitin, starch, polyvinylpyrrolidone or polyvinyl alcohol.

13. The method of claim 9, wherein the active agent is present in the powdered pharmaceutical composition in an amount ranging from about 0.1 to 85 wt % of the composition.

14. The method of claim 9, wherein the powdered pharmaceutical composition is formed using a freeze-drying step.

15. The method of claim 9, wherein the powdered pharmaceutical composition is formed using a spray-drying step.

* * * * *